United States Patent
Christopher et al.

(10) Patent No.: US 10,946,159 B2
(45) Date of Patent: *Mar. 16, 2021

(54) SYSTEM FOR PROVIDING FLOW-TARGETED VENTILATION SYNCHRONIZED TO A PATIENT'S BREATHING CYCLE

(71) Applicant: CS Medical, Inc., Boulder, CO (US)

(72) Inventors: Kent L. Christopher, Denver, CO (US); Stephanie S. Diehl, Littleton, CO (US)

(73) Assignee: CS Medical, Inc., Boulder, CO (US)

( * ) Notice: Subject to any disclaimer, the term of this patent is extended or adjusted under 35 U.S.C. 154(b) by 1088 days.

This patent is subject to a terminal disclaimer.

(21) Appl. No.: 15/415,555

(22) Filed: Jan. 25, 2017

(65) Prior Publication Data
US 2017/0128692 A1    May 11, 2017

Related U.S. Application Data

(63) Continuation of application No. 14/268,234, filed on May 2, 2014, now Pat. No. 9,586,018, which is a
(Continued)

(51) Int. Cl.
*A61M 16/08* (2006.01)
*A61B 5/097* (2006.01)
(Continued)

(52) U.S. Cl.
CPC .......... *A61M 16/085* (2014.02); *A61B 5/087* (2013.01); *A61B 5/097* (2013.01); *A61B 5/4836* (2013.01);
(Continued)

(58) Field of Classification Search
CPC .......... A61M 16/0402; A61M 16/0468; A61M 16/0477; A61M 16/0486
See application file for complete search history.

(56) References Cited

U.S. PATENT DOCUMENTS 9,586,018 B2 *  3/2017  Christopher ...... A61M 16/1095

FOREIGN PATENT DOCUMENTS

WO    WO-2008144589 A1 *  11/2008  ............ A61B 5/097

* cited by examiner

*Primary Examiner* — Jan Christopher L Merene
*Assistant Examiner* — Nathan M Le
(74) *Attorney, Agent, or Firm* — Dorr, Carson & Birney, PC

(57) ABSTRACT

A system selectively delivers either breath-synchronized, flow-targeted ventilation (BSFTV) or closed-system positive pressure ventilation (CSPPV) to augment respiration of a patient with a standard tracheal tube. A removable adaptor has a cap that can be removably attached to the proximal connector of the tracheal tube in BSFTV mode, and an inner cannula that extends within the tracheal tube to effectively divide it into two lumens. The adaptor includes a ventilator connector for removably engaging a ventilator hose to deliver air/oxygen through the adaptor and one lumen of the tracheal tube with a flow rate varying over each respiratory cycle in a predetermined waveform synchronized with the patient's respiratory cycle to augment the patient's spontaneous respiration. The adaptor also includes a port allowing the spontaneously-breathing patient to freely inhale and exhale in open exchange with the atmosphere through the other lumen.

7 Claims, 26 Drawing Sheets

Related U.S. Application Data continuation-in-part of application No. 14/172,696, filed on Feb. 4, 2014, now Pat. No. 9,295,795, which is a continuation of application No. 13/189,956, filed on Jul. 25, 2011, now Pat. No. 8,651,105, which is a continuation of application No. 11/627,512, filed on Jan. 26, 2007, now Pat. No. 8,020,558.

(51) Int. Cl.
| | |
|---|---|
| *A61M 16/00* | (2006.01) |
| *A61M 16/04* | (2006.01) |
| *A61B 5/00* | (2006.01) |
| *A61M 16/12* | (2006.01) |
| *A61B 5/087* | (2006.01) |
| *A61B 5/083* | (2006.01) |
| *A61M 16/06* | (2006.01) |
| *A61M 16/10* | (2006.01) |
| *A61M 16/16* | (2006.01) |
| *A61M 16/20* | (2006.01) |

(52) U.S. Cl.
CPC .... *A61M 16/0051* (2013.01); *A61M 16/0066* (2013.01); *A61M 16/024* (2017.08); *A61M 16/0434* (2013.01); *A61M 16/0465* (2013.01); *A61M 16/0486* (2014.02); *A61M 16/0488* (2013.01); *A61M 16/0666* (2013.01); *A61M 16/0672* (2014.02); *A61M 16/0816* (2013.01); *A61M 16/0833* (2014.02); *A61M 16/0875* (2013.01); *A61M 16/101* (2014.02); *A61M 16/1095* (2014.02); *A61M 16/12* (2013.01); *A61M 16/125* (2014.02); *A61M 16/16* (2013.01); *A61M 16/161* (2014.02); *A61B 5/0836* (2013.01); *A61B 5/6852* (2013.01); *A61M 16/0461* (2013.01); *A61M 16/0484* (2014.02); *A61M 16/10* (2013.01); *A61M 16/208* (2013.01); *A61M 2016/0021* (2013.01); *A61M 2016/0027* (2013.01); *A61M 2016/0036* (2013.01); *A61M 2016/0039* (2013.01); *A61M 2016/1025* (2013.01); *A61M 2202/025* (2013.01); *A61M 2202/0208* (2013.01); *A61M 2202/0275* (2013.01); *A61M 2205/16* (2013.01); *A61M 2205/18* (2013.01); *A61M 2205/32* (2013.01); *A61M 2205/3368* (2013.01); *A61M 2205/502* (2013.01); *A61M 2205/70* (2013.01); *A61M 2230/202* (2013.01); *A61M 2230/205* (2013.01); *A61M 2230/432* (2013.01)

SYSTEM FOR PROVIDING FLOW-TARGETED VENTILATION SYNCHRONIZED TO A PATIENT'S BREATHING CYCLE

RELATED APPLICATION

The present application is a continuation of the Applicant's co-pending U.S. patent application Ser. No. 14/268,234, entitled "System For Providing Flow-Targeted Ventilation Synchronized To A Patient's Breathing Cycle," filed on May 2, 2014, which is a continuation-in-part of U.S. patent application Ser. No. 14/172,696, filed on Feb. 4, 2014, now U.S. Pat. No. 9,295,795, issued on Mar. 29, 2016, which is a continuation of U.S. patent application Ser. No. 13/189,956, filed on Jul. 25, 2011, now U.S. Pat. No. 8,651,105, issued on Feb. 18, 2014, which is a continuation of U.S. patent application Ser. No. 11/627,512, filed on Jan. 26, 2007, now U.S. Pat. No. 8,020,558, issued on Sep. 20, 2011.

BACKGROUND OF THE INVENTION

Field of the Invention

The present invention relates generally to the field of mechanical ventilation of patients. More specifically, the present invention discloses an open system for providing ventilation in a predetermined flow waveform synchronized to a patient's breathing cycle to augment respiration by a self-breathing patient.

Statement of the Problem.

Standard mechanical ventilators deliver pressure. There are three classifications of mechanical ventilators that are based upon how they administer pressure ventilation. Negative pressure ventilation requires an apparatus that expands the chest wall, creating levels of sub-atmospheric pressure that draw air or oxygen-enriched ambient gas through the upper airway and into the lungs. Positive pressure ventilation requires that supra-atmospheric pressure is generated and controlled by the device so that air or oxygen-enriched air is pressurized to the degree that it can be forcibly driven through the upper airway and into the lungs. The third method is a combination of positive/negative pressure. The prime example is a high frequency oscillator, where oscillations of negative and positive pressure are produced in the airway in a sinusoidal pattern that is independent of self-breathing efforts and at a rate that exceeds the maximum human respiratory rate by many fold.

Positive pressure ventilators are by far the most frequently used mechanical breathing device. They can be further divided into invasive or noninvasive systems. Invasive systems utilize an endotracheal or tracheostomy tube, with an inflated tracheal cuff that creates an obstruction closing off the upper airway from atmospheric or ambient gas and thus creates a closed system between the positive pressure ventilator and the lungs. This can be referred to as closed-system positive-pressure ventilation (CSPPV). FIG. 1 shows an example of a conventional tracheostomy tube 80 with an inflatable tracheal cuff 81. FIG. 2 shows an example of a conventional endotracheal tube 90 with an inflatable tracheal cuff 91.

Breath delivery with positive-pressure ventilators can be categorized as either pressure-targeted or volume-targeted ventilation. Generation of a specific airway pressure on inspiration and often a different pressure on expiration are pressure-targeted outcomes, or alternatively, a level of pressure is generated to achieve the primary goal of a targeted tidal volume delivered to the lungs (volume-targeted ventilation). The closed system allows a positive pressure breath to be delivered through the inspiratory valve of the device, through the inspiratory limb of the breathing circuit and directly to the lungs without loss of pressure by dissipation of gas into the atmosphere. The delivery of the breath can be forced into the patient independent of the patient's breathing pattern (time triggering) or synchronized with the patient's effort to inhale (pressure or flow triggering), but the patient's normal negative pressure inspiration during self-breathing is lost as it is converted to a positive pressure breath. Peak inspiratory airway pressures of 20 to 30 cm $H_2O$ or greater are commonly achieved. The inspiratory valve is open during the patient's entire inspiratory phase. During inspiration the expiratory valve on the expiratory limb of the breathing circuit must remain closed to maintain the pressurized breath. The transition from inspiration to expiration is ultimately governed by the ventilator (breath cycling) and not the patient, because in a closed system, the expiratory valve must open to allow exhalation. During exhalation, the inspiratory valve is closed to prevent retrograde flow of gas back into the machine, which could result in the physiologic terms of rebreathing carbon dioxide or dead space gas, which is dangerous and potentially life-threatening. The expiratory valve is at least partially open to allow the breath to adequately vent into the atmosphere. The pressure at the onset of exhalation with CSPPV usually approximates the peak inspiratory pressure (e.g., 20 to 30 cm $H_2O$ or greater) and dissipates over the expiratory phase as a function of the patient's exhaled gas being allowed to exit through the exhalation valve. Though the expiratory valve or mechanism is often completely open during exhalation, partial closure of the expiratory valve or mechanisms during one or more components of the expiratory phase may achieve a targeted level of expiratory pressure within the lungs while still maintaining adequate exhalation through the valve and acceptable gas exchange. Examples of methods to achieve pressure in the lungs during exhalation due to partial exhalation valve closure during one or more points in exhalation include expiratory retard and positive end expiratory pressure (PEEP). During CSPPV, the expiratory valve is not completely closed during exhalation as life-threatening excessive pressure and suffocation could result. Partial closure of the expiratory valve during end exhalation (PEEP) prevents the decline in airway pressure from ever returning to the 0 cm $H_2O$ baseline between exhalation and inhalation. Prescribed PEEP may be 5 to 15 cm $H_2O$ or more. On expiration, with CSPPV all the exhaled gas is routed through the expiratory limb of the circuit and is available to the ventilator for analysis. This analysis is required for proper ventilator function and monitoring. More than one CSPPV mode can be administered simultaneously (e.g., intermittent mandatory ventilation with pressure support and positive-end expiratory pressure).

Though CSPPV can be life-saving for patients who are unable to do any negative pressure self-breathing, there are a number of problems with the CSPPV technology. It has been scientifically demonstrated that the pressure generated by positive pressure ventilation can injure the delicate structures of the lungs. This injury can cause significant morbidity and mortality, particularly when CSPPV is superimposed upon acute lung injury from pneumonia or adult respiratory distress syndrome (ARDS). Over time, positive pressures that were once thought to be safe have been determined to cause lung injury. The safe positive pressure threshold that does not cause (or worsen) acute lung injury on some level is presently unknown. There is a scientific trend for documentation of acute lung injury with lower and lower positive pressures as more is learned about the pathophysiology of acute lung injury on organ, tissue, cellular, biochemical and genetic levels. In certain clinical settings positive inspiratory and/or expiratory pressures may impair gas exchange in the lungs. Positive pressure ventilation can cause life-threatening impairment of cardiac output and can cause lung collapse (tension pneumothorax) resulting from barotrauma.

An endotracheal tube is usually the first tube placed in the trachea to achieve adequate control of the patient's ventilation during the acute phase of respiratory failure. Patients either have no spontaneous breathing efforts, have such compromised respiration that ineffective efforts are insufficient to sustain life, or respiratory collapse is determined to be eminent. On an emergency basis, the endotracheal tube is placed through the mouth, or less commonly through a nostril, and down between the vocal cords and into the trachea. The cuff is inflated to allow CSPPV to be administered to essentially take over breathing as respiratory life support. An endotracheal tube is also commonly placed during induction of general anesthesia for surgery where breathing efforts and muscle control cease. In patients undergoing major surgeries, especially those that have encountered complications, or patients with severely compromised lung function, the endotracheal tube and CSPPV may be required for hours or even days post operatively.

A conventional endotracheal tube (e.g., Mallinckrodt™ Hi-Lo Oral/Nasal Tracheal Tube Cuffed, Murphy Eye, Covidien U.S. Headquarters, 15 Hampshire Street, Mansfield, Mass. 02048) does not allow for communication between the larynx and the upper airway and causes gas to be channeled away from a patient's natural humidification system. The presence of the tube inhibits movement of the vocal cords required for speech. Additionally, the inflated cuff blocks flow of exhaled gas up through the vocal cords to generate speech. Due to the discomfort and impaired communication with CSPPV with an endotracheal tube, patients often require heavy sedation, physical restraint, and occasionally medications to induce muscle paralysis to control agitation and prevent self-harm. Dys-synchrony between the patient's efforts to breathe and the machine's attempt to deliver the breath results in impaired ventilation and this problem is more deleterious with patient agitation. On the other hand, suppression or abolition of the patient's breathing efforts by muscle paralytic agents and/or heavy sedation may cause deterioration of respiratory muscle strength. The experience of treatment of critical respiratory illness with CSPPV, particularly with the limitations with an endotracheal tube, can be associated with post-traumatic stress disorder (PTSD) in survivors.

Though there are substantial discomforts and problems with CSPPV administered by a standard endotracheal tube, the life-saving (life support) benefits of being able to totally take over the patient's breathing for the short-term often out way the risks. The goal is to eliminate the need for CSPPV and remove the endotracheal tube. Once the patient becomes more medically stable, has reduced sedation requirements, begins to recover alertness, exhibits resumption or improvement in spontaneous breathing efforts, and begins to recover lung function, alternatives to CSPPV with the endotracheal tube can be considered. One option is to take the chance and remove the endotracheal tube, thus discontinuing CSPPV. Though further risk of associated discomforts/complications may be avoided, failure due to premature discontinuation creates another cycle beginning with another emergent endotracheal tube placement and life-sustaining ventilation. This is not uncommon. This disclosure presents another alternative to further manage recovering self-breathing patient utilizing the same CSPPV endotracheal tube adapted with a method and apparatus to administer flow-targeted ventilation synchronized with the patient's breathing cycle, or breath-synchronized flow-targeted ventilation (BSFTV). This process fosters recovery from respiratory failure and facilitates liberation from ventilatory support and the endotracheal tube. Utilization of the same endotracheal tube avoids substantial potential risk of removing one style of tube and inserting another. The patient may then be managed with a dedicated ventilator that administers BSFTV. Alternatively, a system of methods and devices are disclosed to enable utilization of a ventilator that has the capability of delivering CSPPV and then seamlessly facilitate liberation using BSFTV.

Presently, patients with an endotracheal tube that cannot be liberated successfully from high level CSPPV support undergo a surgical procedure wherein a tracheostomy tube replaces the endotracheal tube to deliver CSPPV. This is often considered within a range of 7 to 14 days. Surgical placement of tracheostomy tubes can result in a number of complications, including bleeding, infection, barotrauma and airway obstruction. Placement of the tracheostomy tube does not avoid the described complications and discomforts directly associated with continued use of positive pressure ventilation. Inadvertent dislodgement of the tracheostomy tube or failed attempts to replace the tube before adequate surgical healing of the tract occurs can result in a high risk airway emergency.

A standard tracheostomy tube (e.g., SHILEY™ Adult Tracheostomy Tube Cuffed Single Cannula, Covidien U.S. Headquarters, 15 Hampshire Street, Mansfield, Mass. 02048) frees up the upper airway and is more comfortable, but the cuff must still be inflated to deliver pressurized breaths. The inflated cuff prohibits utilization of the vocal cords. Patients are unable to speak causing poor communication between the patient and healthcare providers and family thus impeding proper informed consent and establishment of advanced directives. Similar to an endotracheal tube, this absence of speech can cause frustration, anxiety and depression. Bypassing the larynx also impairs coughing. Normal closure of the vocal cords allows generation of a glottic blast that facilitates effective cough and clearance of respiratory secretions. Finally, the vocal cords serve as a variable regulator of respiratory flow that fine tunes passage of gas in and out of the lungs to optimize gas exchange.

As with CSPPV via an endotracheal tube, continued CSPPV via a tracheostomy tube is often required when the patient has not adequately recovered with enough medical stability and self-breathing capability to be liberated from CSPPV. Again, over this period of time, aggressive CSPPV life-support outweighs the discomforts and risks. Similarly, premature termination and removal of the tracheostomy tube has high risk, particularly when the surgical tract for the tube has not healed, and reinsertion or exchanging the tracheostomy tube can be hazardous.

Liberating patients from CSPPV delivered by either an endotracheal tube or tracheostomy tube requires a successful return of the patient to normal negative pressure self-breathing. This has proven to be difficult, particularly when patients have had their breathing controlled and altered by CSPPV for greater than 21 days (prolonged mechanical ventilation, or PMV). In fact, once patients have required CSPPV for greater than 21 days, the CSPPV liberation success rate is only about 50% overall, with a range of 35% to about 60%. Patients are subject to discomforts and risks of CSPPV over this prolonged period of attempted liberation, even when a tracheostomy tube is placed.

The prior art also includes ventilation systems based on "flow triggering" a breath that is subsequently supported by CSPPV. As opposed to a drop in circuit/ventilator pressure indirectly indicating a breath effort by a patient, the CSPPV breath is triggered by a presumed effort by the patient to generate inspiratory flow. Though patient inspiratory flow is not directly measured, the breathing effort is presumed because flow inside the expiratory limb is measured to drop to less than the known pass through, or bias flow through the circuit. Flow triggering requires a dual inspiratory/expiratory limb circuit. At some point in the mid to late expiratory phase, the ventilator delivers a predetermined constant flow that circulates through the inspiratory and expiratory limb of the circuit and out through the open expiratory valve. With flow triggering the inspiratory valve or mechanism is partially open in the transition phase between exhalation and inhalation, allowing low flows concurrent with the patient's inspiratory effort to enhance triggering sensitivity of the machine. Flow is measured at both the proximal connection of the inspiratory limb and near the expiratory valve. Any drop in flow is assumed to represent the patient's effort to breathe in gas, and the inspiratory breath is triggered. Though flow through the ventilator circuit may reduce the work the patient has to do to draw in an initial portion of the breath to trigger the ventilator, the delivered breath is still positive pressure generated and is either pressure or volume targeted.

Another technology that utilizes a catheter placed within a cuff-inflated tracheal tube during concurrent CSPPV is called Tracheal Gas Inflation (TGI). TGI is different than the present invention because, in addition to a delivered CSPPV mode used to deliver a positive-pressure breath via the tracheal tube with an inflated cuff, an additional flow of gas is insufflated into the trachea via a catheter placed within the tracheal tube. As with High Frequency Jet Ventilation (HFJV) delivered with CSPPV as discussed below, a second source of gas is supplied via a second lumen, and gas that exits the patient must exit the exhalation valve. The exhalation valve is partially or completely open during exhalation. With TGI, the second lumen delivers standard CSPPV breaths concurrent with flow through the tracheal catheter. Thus, TGI is a mode delivered in conjunction with one or more CSPPV modes.

One very different type of CSPPV mode is High Frequency Jet Ventilation (HFJV). A pulsating (non-continuous) jet is delivered via a catheter placed within a tracheal tube with inflated cuff. The pulsing volume is determined by setting a driving pressure in pounds per square inch (e.g., 30 psi) and the set rate is multiples of the patient's breathing rate (e.g. 150 breaths per minute) and not synchronized with the patient's efforts. A second source of gas flow is available from the ventilator circuit that can be drawn into the tracheal tube directly through the patient's breathing efforts or indirectly drawn in by a venturi effect from flow through the interconnected HFJV device. Gas that passes through the CSPPV circuit and past the patient's airway must exit through, at minimum, a partially open exhalation valve. Gas exhaled by the patient must also exit via the exhalation valve.

HFJV is different than the present invention for a number of reasons. First, it is a form of Positive Pressure Ventilation (PPV) (i.e., pressure-targeted). Gas is delivered in discreet boluses in a rapid manner not synchronized with the patient respiratory cycle. It is a closed system with the exhalation valve partially or completely open during exhalation. Finally, a second lumen is required to deliver additional flow to the patient.

Transtracheal augmented ventilation (TTAV) is a prior art system that provides an alternative to positive pressure ventilation. TTAV is not intended to give full ventilatory support like a CSPPV device, but augments the patient's self-breathing by utilizing an open system and delivering a constant and continuous flow of about 8 to 20 L/min of a heated and humidified air and oxygen blend to the lungs during both inspiration and expiration. It is an open system because there is no inflated tracheal cuff and no mask, nasal pillows or other device to create a complete or near complete barrier between the mouth and/or nose and the atmosphere. Because of the nature of the open system, delivered gas can easily escape into the atmosphere and positive pressure is not a targeted outcome. Tidal volume that the patient inspires through the device is not an outcome that can be reliably targeted because of volume loss through the upper airway and variability of volume that the patient inspires through the upper airway during negative pressure self-breathing. In fact, TTAV is only intended for use on patients who are able to do some degree of negative pressure self-breathing. Benefits from augmented ventilation are derived from a defined constant and continuous flow that is superimposed upon the patient's own breathing cycle. Patients can freely inhale room air through the mouth and nose in addition to the gas delivered by the TTAV device. With prior art, air or oxygen enriched air can be delivered directly into the trachea via a transtracheal catheter. The delivery device heats and humidifies the gas to eliminate complications and sequellae from the humidity deficit that would otherwise occur from delivering constant and continuous flows of 8 to 20 L/min of dry cool gas directly into the trachea. There is a single inspiratory circuit with no expiratory circuit or expiratory valve because the patient is free to exhale normally through the nose and mouth. No inspiratory valve is used as a constant and continuous flow is delivered to the patient rather than distinct breaths. Since the constant and continuous flow is superimposed upon the patient's inherent negative pressure self-breathing cycle, synchronization with the patient's breathing is not required. A pressure relief valve prevents over-pressurization within the device in the event of a malfunction or obstruction and an alarm signals the event. Exhalation of gas back into the breathing circuit or into the device is not required to monitor or manage gas delivery during routine operation.

Compared to either low flows used with prior art transtracheal oxygen therapy or mouth breathing without transtracheal flows, potential physiologic benefits of TTAV at a constant continuous flow of 10 L/min include correction of hypoxemia, reduced inspiratory work of breathing, decreased volume of gas the patient must inspire through the upper airway, and improved exercise capacity. The effect of constant continuous TTAV flow above 10 L/min corrects hypoxemia. Since prior studies show that the relationship between flow and response is directly related, one would predict improved response in terms of reduced inspiratory work of breathing, decreased volume of gas the patient must inspire through the upper airway, and improved exercise capacity with flows above 10 L/min. However, the effect on these specific physiologic parameters has not been specifically evaluated. Compared to low flow transtracheal oxygen therapy at 1.5 L/min, potential physiologic benefits of TTAV at a constant and continuous flow of 15 L/min additionally include increased efficiency of breathing, reduced total minute ventilation and reduced end-expiratory lung volume. The effect of constant and continuous TTAV flow above 15 L/min on these physiologic parameters has not been evaluated. Reduced physiologic dead space is seen with low flow transtracheal oxygen (up to 6-8 L/min) as compared to mouth breathing. However, it is not known if constant and continuous flow above 8 L/min with TTAV results in any further reduction in physiologic dead space. TTAV at 10 L/min as a means of augmenting ventilation of patients with chronic respiratory failure during nocturnal home use has been shown to be safe and effective.

As noted, TTAV can be administered via a catheter placed directly into the trachea. However, TTAV has been used to facilitate liberation of CSPPV patients from prolonged mechanical ventilation. Self-breathing patients are briefly disconnected from the CSPPV system, and the existing standard sized and designed CSPPV tracheostomy tube is replaced with a smaller tube with fenestrated openings on the posterior wall of the tube. An inner cannula without fenestrations is inserted and the tracheostomy cuff is again inflated, allowing leak free CSPPV. For liberation attempts, in an iterative basis for longer and longer periods, CSPPV is removed, the cuff is deflated and the inner cannula is removed. A separate TTAV gas delivery device is used and the TTAV catheter fitted with an air tight cap is inserted into the tracheostomy tube lumen and the cap is tightly secured to the 15 mm connector of the tracheostomy tube opening. The catheter delivers a constant and continuous TTAV flow from 10 to 15 L/min through the tracheostomy tube while the patient is allowed to self-breathe in and out through the fenestrations and between the outside of the tracheostomy tube and airway wall. However, with the tight-fitting cap that contains the transtracheal catheter on the proximal (atmospheric) end of the tracheostomy tube, the patient is unable to self-breathe into the atmosphere through the tracheostomy tube opening. With open fenestrations and the cuff deflated while the patient is on the TTAV device with a constant and continuous flow, all gas is expired through the vocal cords, and upper airway resulting in described benefits associated with restored speech, more effective cough and return of vocal cord function as a physiologic variable regulator of respiratory flow. TTAV has been shown to improve liberation success from CSPPV. It is unknown if constant and continuous TTAV flow above 15 L/min improves effectiveness or wean outcome.

A less than optimal condition associated with TTAV is that a constant and continuous flow is administered throughout the inspiratory and expiratory phases of the respiratory cycle. Each of the potential benefits as described above will likely have different respiratory cycle targeted flow rates and waveforms to achieve maximal beneficial effect in a given patient, and requirements may change with alterations in the clinical status of that individual over time. Additionally, patients with different diseases or disorders may benefit more from certain physiologic effects than from others, and those effects can be influenced by different flows and flow waveforms administered in specific phases (or phase components) of the respiratory cycle. Synchronizing the amount and pattern of flow with specific phases of the breathing cycle or even components of phases of the breathing cycle may markedly influence clinical efficacy. In contrast, constant continuous flows delivered throughout the inspiratory and expiratory phases as seen in the prior art may not be efficacious. For example, a constant and continuous flow of 40 L/min delivered throughout the inspiratory phase of breathing may significantly increase total inspiratory work of breathing rather than reduce it if the specific physiologic effect on the respiratory inspiratory phase and phase transitions as well as the phase components are not considered. With prior TTAV art, that constant and continuous flow of 40 L/min would also be delivered during exhalation. That amount of flow throughout expiration would likely impose a significant expiratory workload causing the patient to forcibly exhale against the constant incoming stream of tracheal gas. This could result in respiratory muscle fatigue and impaired gas exchange. There may be benefit to transiently interrupting flow during certain components of the breathing cycle which could influence clinical efficacy. TTAV with a constant and continuous flow eliminates the potential for improving safety, efficacy and tolerance by the inability of the prior art to target non-constant, potentially non continuous flows with different peak flows and flow patterns that are strategically synchronized with the various phases or components of the phases of a patient's breathing cycle. Another potential drawback of present TTAV practice for CSPPV liberation is that the CSPPV tracheostomy tube must be removed and replaced with the smaller TTAV tracheostomy tube with a different design including fenestrations to allow self-breathing when the above-described catheter is used.

Another weakness associated with conventional TTAV systems is that, other than an alarm and pressure relief valve for excessive pressures encountered within the channels of the delivery device and lumen of the circuit, there are no sensors or measurement devices that provide physiologic data that identify phases or components of phases of the patient's negative pressure self-breathing cycle that are designed to regulate breath synchronized, flow-targeted delivery. Conventional TTAV systems do not have microprocessors supporting breath-synchronized, flow-targeted delivery designed to manage patient physiologic data, display the data, trigger alarms for out of range results or incorporate that information into intelligent processing for a feedback loop or servo controlled device response to the physiologic data. Another problem with conventional TTAV systems is that the only clinical implementation to date has been limited to use with a transtracheal catheter.

Freitag (U.S. Pat. Nos. 7,487,778, 7,533,670 and 8,631,797) has disclosed an ambulatory oxygen system with a wearable "ventilator" pump weighing about one pound and a companion small oxygen cylinder for use in patients with severe lung disease. Freitag describes a small gas delivery catheter surgically placed in the trachea with the preferred embodiment also having a jet nozzle at the distal end to give extra velocity out the catheter tip. The catheter may be secured in the tracheal airway limited to, and abutting against a segment of the tracheal wall circumferentially, and a Montgomery tube is given as an example. The catheter may be either secured at one discrete point along the stabilizer with the catheter length oriented along the longitudinal axis of a discrete segment of the tracheal stabilizer. Alternatively, designs without the stabilizer are disclosed for securing devices at right angles to the outer catheter wall to abut up against the tracheal mucosal wall to maintain the catheter and catheter flow down the center of the trachea. Only catheters are disclosed as gas delivery devices. A catheter with embodiments of a system for respiratory support as limited to that inventors' disclosure may be passed through the mouth or nose into the trachea. Features of either a tracheostomy tube inserted directly through an opening in the trachea or endotracheal tube passed through the nose or mouth, both with a cuff that is inflatable are not disclosed. The support structure is not identified as either a tracheostomy or endotracheal tube as separation between the structure and the trachea is not disclosed, and no inflatable cuff for CSPPV is disclosed. Self-breathing with the tracheal catheter does not occur through the surgical tracheal opening as with a tracheostomy tube or through an endotracheal tube, but only around the catheter and through the normal anatomy of the upper airway. Catheters may have an additional channel, but it is also designed for gas delivery, and channel shutters can be adjusted to direct flow out of circumferential ports along the longitudinal axis in either a cephalad (upward) or caudal (downward) flow direction. Freitag does not disclose a system that can alternatively deliver CSPPV either with or without a standard tracheostomy or endotracheal tube.

Another problem is that CSPPV devices are only configured to deliver positive pressure ventilation, and are not configured to alternatively deliver BSFTV with an open system. This would be a clinical advantage, if switching from one delivery method to the other in a given patient, in a strategy to improve patient comfort and clinical outcomes, did not also require switching out ventilator devices. Utilization of one ventilator versus two ventilator designs would improve logistics of resource planning and utilization, and reduce clinician time in ventilator management, capital costs and equipment maintenance.

Solution to the Problem

The present invention provides a ventilator system for selectively delivering either breath-synchronized, flow-targeted ventilation (BSFTV) to augment the respiration of a self-breathing patient, or closed-system positive-pressure ventilation (CSPPV) using the same tracheal tube. Patients without spontaneous breathing or with insufficient spontaneous breathing can be managed with the CSPPV mode. Patients with sufficient spontaneous breathing, but who can not entirely negative pressure self-breathe without ventilator support can benefit from the BSFTV mode. BSFTV delivers a predetermined flow waveform to the patient's airway in synchronization with the patient's breathing cycle and at a sufficient flow rate to achieve a desired physiologic outcome, such as mitigating pressure in the patient's airway, reducing the patient's work of breathing, flushing carbon dioxide from the patient's airway, and increasing blood oxygenation.

For some situations, such as single patient home use, a dedicated BSFTV system may be optimal. However, there are advantages to utilization of the present system which employs integration of the functionality of CSPPV and BSFTV devices. For example, one advantage of combining the present BSFTV system with PPV in one device is the reduction of clinician time in ventilator management and elimination of the steps of switching the patient back and forth between two separate ventilator devices to achieve a needed clinical outcome. Another advantage is the avoidance of the clinical risk of replacing the tracheal tube with a different design. Finally, the present invention has the advantage of elimination of need for capitalization of a separate CSPPV and BSFTV device. This controls cost, reduces redundancy of delivery devices, increases efficiency, saves space at the patient bedside and improves resource allocation. With increasing pressures for cost containment in the healthcare industry, broad-based use of capital equipment, such as ventilators incorporating the present invention, offers substantial cost-saving potential. Use of the present dual functionality ventilator would have economic merit, even if an individual patient may only need one mode for the duration of his or her care.

A benefit of the present invention is that the disclosed patient interfaces can adapt conventional cuffed tracheal tubes used to deliver standard CSPPV to alternatively deliver BSFTV. In addition, a major clinical advantage of the present invention is that it enables delivery of BSFTV using servo-controlled feedback from physiologic sensors for auto-titration of the initially selected delivered gases and flow waveforms through monitoring the breath delivery to achieve clinician-targeted physiologic ventilatory outcomes within the clinician-defined BSFTV delivery parameters. Each of the above solutions should improve access of certain patient populations to the medical benefits of the present invention.

The present system is intended to augment ventilation by superimposing continuous, non-constant and, under some conditions, non-continuous flows upon the spontaneous self-breathing of patients. Unlike prior art pressure-targeted or volume-targeted positive pressure ventilation, this invention is flow-targeted because achievement of specific flows and flow waveforms are the targeted outcome. Clinician-defined flows are targeted for specific phases or components of phases of the patient's breathing cycle in order to achieve one or more physiologic improvements. Unlike CSPPV, where positive pressure is either the targeted endpoint or an expected consequence of volume-targeted ventilation, the present invention uses an open system and avoids generation of positive pressures that can cause patient discomfort and injury. A variety of sensors can be used to detect properties associated with phases and phase components of the patient's breathing cycle. A microprocessor receives and processes the data generated by the sensors for intelligent monitoring and regulation of the present system. With physiologic feedback from the patient's respiratory sensors, the microprocessor can auto-adjust multiple properties including the initial clinician-selected waveform delivery of the breath synchronized flow targeted breathing to meet clinician-determined physiologic outcomes. Additionally, the microprocessor can govern delivery limits and associated alarms and alerts set by clinicians for data out of clinically predetermined range.

In the presence of respiratory distress, the present invention mitigates the negative-pressure swings that the patient with respiratory compromise must generate during inspiration and the positive-pressure swings that must be generated during expiration with certain diseases and disorders. These pressure swings result from increased work of breathing (WOB). The present system can mitigate the patient requirement for generating pressure, and can thus mitigate excessive WOB, while still allowing the patient to self-breathe in an open system without the need for CSPPV.

The present invention enables modification of conventional ventilator designs to also provide BSFTV (i.e., to have the capability of delivering either positive pressure ventilation or BSFTV), with the additional benefit of enabling servo controlled feedback from physiologic sensors to auto-titrate parameters such as the initially clinician-selected flow waveform and monitor the breath delivery to achieve targeted physiologic outcomes set by the clinician.

SUMMARY OF THE INVENTION

This invention provides a system to selectively deliver either breath-synchronized, flow-targeted ventilation (BSFTV) or closed-system positive pressure ventilation (CSPPV) using a standard tracheal tube, such as a tracheostomy tube or an endotracheal tube. Though there are substantial discomforts and risk of complications with CSPPV, patients without spontaneous breathing or with insufficient spontaneous breathing must be managed with the CSPPV mode. Patients with sufficient spontaneous breathing, but are unable to self-breathe without ventilatory assistance can benefit from the BSFTV mode.

In BSFTV mode, an adaptor with a cap is removably attached to the proximal connector of the patient's tracheal tube, and an inner cannula that extends within the tracheal tube, effectively divides the tracheal tube into two lumens. The adaptor cap includes a ventilator connector for removably engaging a ventilator hose to supply air/oxygen to the patient's tracheal tube through either: (1) the inner cannula; or (2) the annular region between the exterior of the cannula and the interior of the tracheal tube. The adaptor cap also includes a port allowing the patient to freely inhale and exhale in open exchange with the atmosphere through the other lumen.

In BSFTV mode, a sensor detects a physical property of a patient's respiratory cycle. A processor monitors the sensor and controls a gas source to deliver oxygen-containing gas through an adaptor and tracheal tube extending into the patient's airway with the flow rate varying over each inspiratory and expiratory phase of the respiratory cycle in a predetermined non-constant waveform synchronized with the respiratory cycle to augment the patient's spontaneous respiration. Gas is delivered at a flow rate sufficient to significantly mitigate the airway pressure the patient must generate during spontaneous breathing and thereby reduce the patient's work of breathing.

CSPPV mode can be provided in the conventional manner with the adaptor removed and the ventilator hose of the "y" or "wye" of the circuit connected directly to the proximal connector on the patient's tracheal tube. In both modes, the tracheal tube with an inflatable cuff remains in place in the patient airway.

Thus, the present invention can smoothly and safely transition patients requiring CSPPV with a standard endotracheal or tracheostomy tube, thus reducing exposure to further risks, discomforts and complications of CSPPV, and facilitating liberation of the patient from ventilator support and back to autonomous self-breathing. The present system enables modification of a BSFTV ventilation system to provide the capability of delivering either positive pressure ventilation or BSFTV. To achieve additional financial and patient care logistic benefits, particularly in some hospitalized patients, this serves as an alternative to utilization of a dedicated BSFTV system.

The present invention can also include servo-controlled feedback from physiologic sensors to auto-titrate the delivered gases and initially prescribed flow waveforms while monitoring the breath delivery to achieve targeted physiologic ventilatory outcomes.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

As previously discussed, the present invention provides a system to selectively deliver either breath-synchronized, flow-targeted ventilation (BSFTV) or closed-system positive pressure ventilation (CSPPV) to augment respiration by a patient with a standard tracheal tube, such as a tracheostomy tube or an endotracheal tube. In particular, the ability to use the present invention with standard cuffed tracheostomy and endotracheal tubes makes it convenient, efficient and both clinically effective and cost-effective to provide open-system breath-synchronized flow targeted ventilation (BSFTV) via the trachea. Similar benefits can be achieved if a ventilator system is utilized that allows a ventilator to selectively administer either CSPPV or BSFTV, without requiring replacement of the patient's existing conventional tracheal tube.

System Overview.

Figure 3:
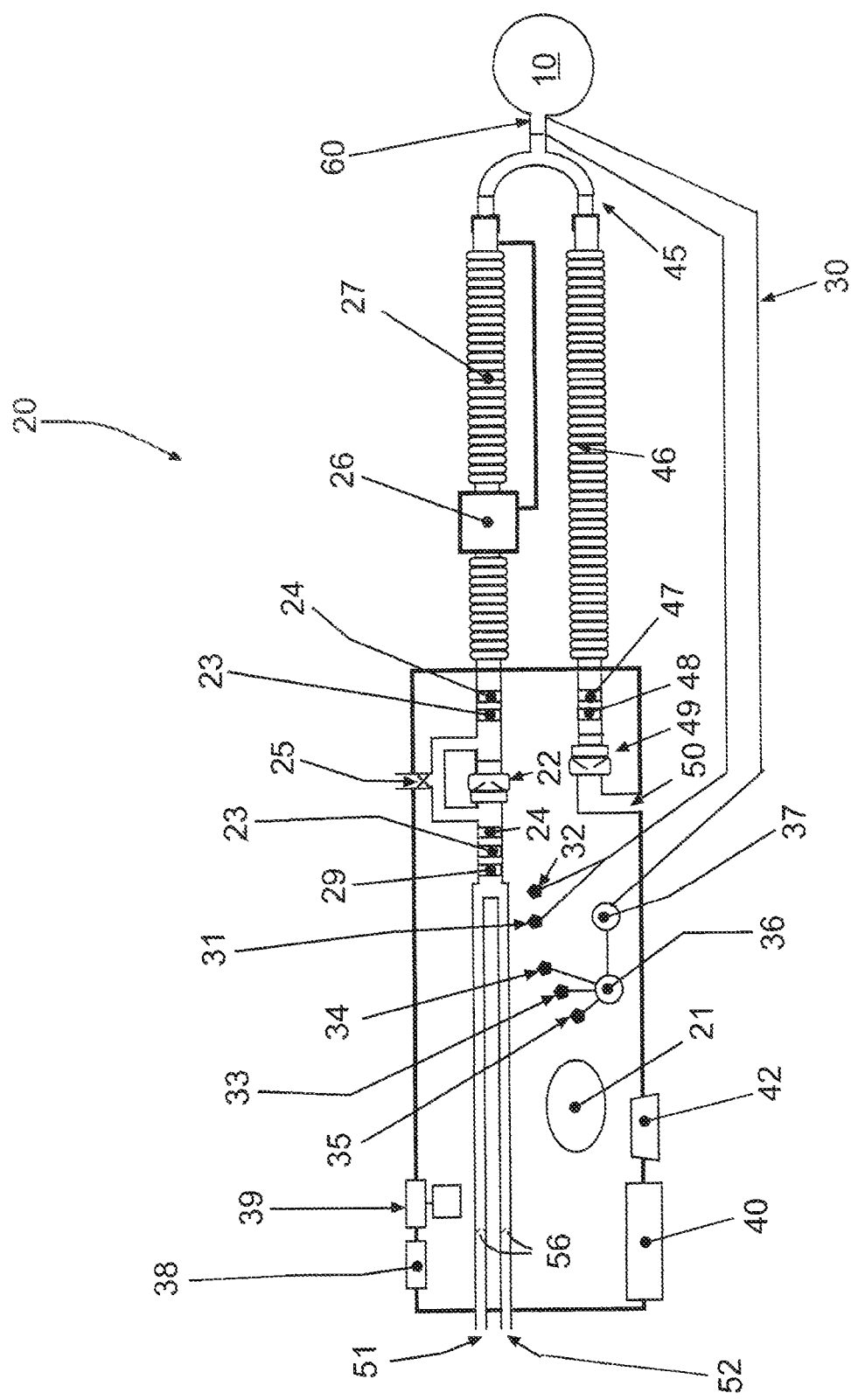
FIG. 3 is a simplified diagram of the present system in which a ventilator 20 has been modified to alternatively deliver CSPPV or BSFTV via a tracheal tube 60.

FIG. 3 is an illustration of a basic configuration of the present system using a ventilator 20 that has been modified to alternatively deliver either CSPPV or BSFTV. In particular, the ventilator 20 in FIG. 3 has been modified to utilize a standard CSPPV dual-limb ventilator circuit comprised of an inspiratory limb 27 and an expiratory limb 46 with an interposed "Y" or "wye" connector 45 attached to the ends of standard 22 mm circuit connections. The joined lumen connects to a standard 15 mm tracheostomy or endotracheal connector 60 attached to the patient 10.

In the preferred embodiment, oxygen-containing gas is delivered by the ventilator to the patient through a servo temperature-controlled humidifier 26 with a heated breathing circuit 27 that delivers gas within an approximate predefined temperature range (approximately 34-38° C.) and relative humidity (approximately 70 to 100%). The circuit 27 may be heated by a wire, circulating heated water or air, or similar means or the tubing may be insulated by a chamber of air or other means. The heated/humidified circuit 27 on the inspiratory limb of the ventilator circuit is connected to the expiratory limb through the "Y" or "wye" connector 45. The base of the "Y" connector is comprised of a short ventilator hose 28 with connector that attaches to standard 15 mm connections either directly to the patient airway interface 60 (e.g., tracheostomy tube or endotracheal tube) with the CSPPV mode, or indirectly through the adaptor 70 used with the BSFTV mode, which will be discussed below.

Oxygen-containing gas can be made available to the delivery system from a variety of external sources. For example, sources 51 may include, but not limited to piped wall oxygen, direct liquid or compressed gaseous oxygen source, or an oxygen concentrator. Additionally, an external source 52 of air (such as piped wall air, direct air compressor or blower source) or other medical gases including, but not limited to helium or nitric oxide (by a variety of delivery means) could be used. In another embodiment, an air compressor, blower or similar air source can be housed within the present system. Though not limited to this application, these embodiments would likely be used in a hospital or similar institutional setting.

In another embodiment, oxygen is supplied by an internal oxygen concentrator or comparable oxygen generating device that is housed within the present system. Additionally, an air compressor or blower or similar air-generating device is housed within the present system. This embodiment could be used in either the home or a hospital, nursing home or similar institutional setting.

Finally, an internal air compressor, blower or other air supply can be combined with external delivery of oxygen into the proximal inspiratory limb of the circuit 27 via a T-connection or an equivalent connection. Sources could be (but not limited to) an external compressed oxygen gas cylinder or liquid oxygen source or oxygen concentrator. This embodiment may be most appropriate for a setting such as the home or nursing home setting.

In any case, the gas composition from those respective sources is regulated by one or more gas supply valves. Concentrations of gas delivery can be confirmed by analyzers 29 for the appropriate source such as oxygen, helium or nitric oxide. The inspiratory valve 22 noted in FIG. 3 regulates the maximum or peak flow and the associated flow waveform under the control of the processor 21, which monitors and regulates the valve through flow sensor 24. Pressure transducers 23 can be placed proximal, distal or preferably both proximal and distal to the inspiratory valve 22. A pressure transducer 23 or other pressure sensing/measuring device is preferably located proximal to the inspiratory valve 22 to measure pressure and detect excessive machine pressure. Additionally, the preferred embodiment also incorporates a pressure transducer 23 or other pressure sensing/measuring device that is preferably located distal to the inspiratory valve 22 to measure pressure and detect excessive pressure within the flow delivery circuit. As shown in FIG. 3, a conduit before and a conduit after the inspiratory valve merge into a conduit that has a pressure relief valve 25 that vents to the atmosphere, preventing excessive pressure build up within the present device or within the gas delivery circuit. Other configurations accomplishing the same outcome apply. Data from all of the sensors, valves, monitoring, measurement devices or other systems are passed on to the processor 21 and the processor 21 is preferably in bidirectional communication with those devices and multiple communications can occur simultaneously among the processor 21 and other systems. The expiratory limb 46 of the ventilator is a conduit for the patient's exhaled gas in the CSPPV mode of operation. The conduit enters the ventilator and typically connects to a pressure-sensing device 48 to directly or indirectly measure pressure within the conduit. Exhaled gas also passes through a flow sensing device 47 that measures the patient's exhaled flow. The measured flow can be integrated into volume by processor 21. In line is a valve 49 that governs the exit of the exhalate from the ventilator and into the atmosphere. Complete or partial closure of the valve may occur prior to full exhalation to maintain required expiratory pressure, such as positive end expiratory pressure (PEEP), which has been previously discussed and is commonly used with CSPPV. An in-line air filter is typically present that filters the exhalate before it exits the ventilator through port 50 and is discharged into the atmosphere.

Delivery, monitoring and management of CSPPV is governed by processor 21 with associated audio alarms 42 and a graphic user interface (GUI) 40 with all the functionality and visual displays and visual alarms used in CSPPV. The different options discussed above for collection, blending and monitoring of a variety of oxygen-containing gases and individual gas concentration measurement 29 are maintained.

Related to the inspiratory portion of the ventilator 20, an inspiratory valve, flow sensors, pressure sensors, other sensors and a means of mixing, filtering and measuring delivered gas concentration occurs, all controlled, monitored and managed by a processor 21. In fact, the spectrum of CSPPV delivery modes and settings, selected and integrated with GUI 40 and alarm 42 options are controlled by the processor 21. The sensing, monitoring and management by processor 21 for initiation of the positive-pressure breath delivery by identification of the inspiratory phase by pressure, flow triggering or any other method such as time triggering are maintained functionality through processor 21. The processor manages and monitors the devices on the inspiratory component of the ventilator to deliver the pressure-targeted or volume-targeted positive-pressure breath delivery or combination thereof, that are user-selected from all the optional modes and settings available for CSPPV.

As with other dual-limb ventilator circuit use, the expiratory valve 49 remains closed during inspiratory breath delivery, to maintain the required positive pressure to drive, through the closed system, passage of the ventilator delivered inspired gas through the patient interface 60 and into the lungs of patient 10. The processor 21 monitored pressure, volume and time meters allow it to identify the point for breath delivery termination established by the user, by closing the inspiratory valve 22.

Concurrent with the processor 21 closing of the inspiratory valve after the breath is delivered, opening of the expiratory valve 49 allows for exhalation through the expiratory circuit and expiratory conduit of the ventilator, and exhalate exits the ventilator through port 50 and is discharged into the atmosphere. The processor 21 monitors diminishing positive pressure during exhalation, for example, with pressure transducer 48. If a PEEP in cm $H_2O$, or any other level of pressure is to be established during exhalation as selected by the user, the exhalation valve closes proportionately or completely as required and the pressure is achieved and monitored by processor 21 until the next breathing cycle begins.

During delivery of CSPPV, the processor 21 disables any and all sensors specifically required by BSFTV, but not required by CSPPV, whether within the adaptor 70, the patient interface 60, the circuit, the ventilator 20, or interfacing or intermediate device. This includes any BSFTV-dependent aspiration systems 36, purge pumps 37 or similar technology that is not required for fully functional CSPPV. Any processor 21 displays that are passed through to the GUI 40 or audible alarms 42 for BSFTV would be disabled in this configuration. However, the GUI option to return to BSFTV and disable CSPPV would be active.

Figure 4:
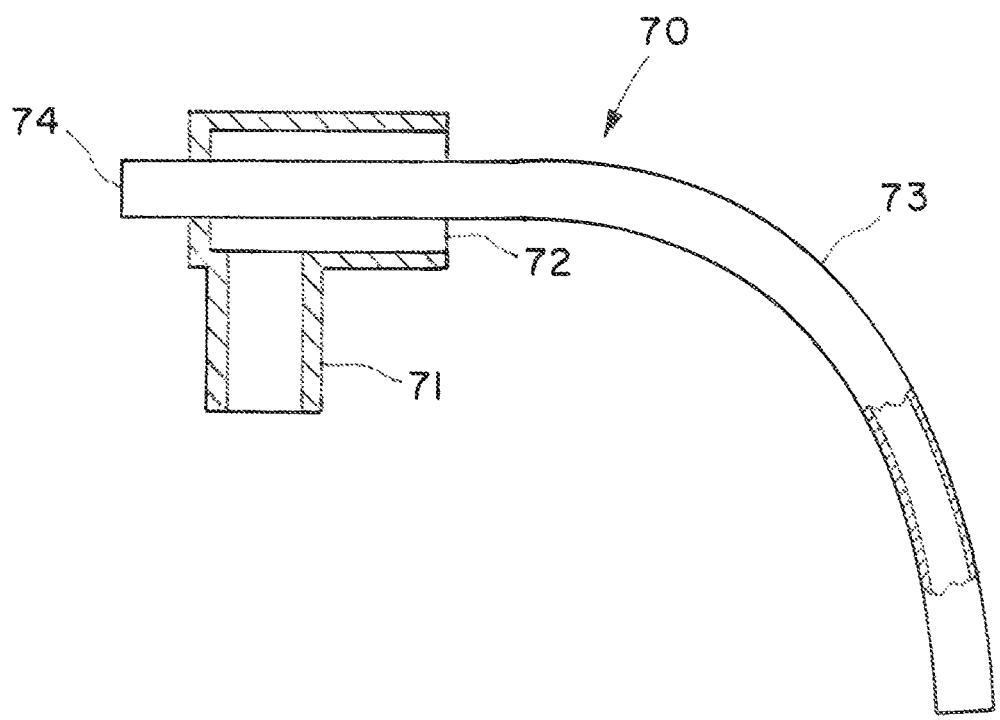
FIG. 4 is a vertical cross-sectional view of the adaptor 70 used in the present invention.

In BSFTV mode, the processor 21 uses flow sensor 24 to control the inspiratory valve 22 to deliver a flow of oxygen-containing gas through the inspiratory limb, adaptor 70 and tracheal tube 60 to augment the patient's spontaneous respiration. Other devices utilized by the processor 21 during CSPPV remain functional as appropriate to manage and monitor the properties of the gas delivery to the patient. Safety systems for preventing failure resulting in undesired back pressure remain active as well. As previously discussed, in BSFTV mode, this flow varies over the inspiratory and expiratory phase of the patient's respiratory cycle in a predetermined non-constant flow waveform synchronized with the respiratory cycle. Typically, the expiratory valve 49 is closed during the expiratory and inspiratory breath cycle in BSFTV mode, since the patient can freely exhale through the adaptor 70 attached to the proximal end of the patient interface 60 (e.g., tracheostomy tube or endotracheal tube), as will be discussed below. In other words, the present invention functions as an open system for ventilation in BSFTV mode. Similarly, related expiratory sensors and feedback to the processor 21 are unnecessary, and can be disabled. Alternatively, the expiratory sensors may be engaged by the processor 21 to achieve, with alternative connectivity measures, sensor functionality required for BSFTV relating to adaptor 70. Alternatively, pressure sensor 47 and valve 49 could function as a safety backup relief for pressure sensors 23 and relief valve 25 for inadvertent excessive pressure build up in the system, including the patient's airway The patient airway interface 60 may include any of a variety of conventional tracheal tubes placed within the patient's airway, including, but not limited to a tracheostomy tube 80 or an endotracheal tube 90. An adaptor 70, as shown for example in FIG. 4, is removably attached to the standard proximal connector of the tracheal tube to serve as a temporary interface in BSFTV mode between the tracheal tube and the ventilator 20. The adaptor 70 includes a smaller-diameter cannula 73 that slides into the tracheal tube, and thereby divides the tracheal tube into two lumens. One lumen is used to supply oxygen-containing gas from the ventilator 20 to the patient, while the second lumen allows the spontaneously-breathing patient to freely inhale and exhale in open exchange with the atmosphere through a port in the cap of the adaptor. The system can be returned to CSPPV mode by removing the adaptor 70 while leaving the tracheal tube in place, and then reconnecting the ventilator hose 28 to the proximal connector of the tracheal tube.

The adaptor 70 for the patient airway interface 60 may have a number of sensors 75 or gas sampling tubings 77 that can be attached or integrated into the inside or outside wall of the adaptor tube 73, so that the processor 21 can monitor the patient's self-breathing and synchronize the flow of gas supplied to the patient in BSFTV mode accordingly. Additionally, to monitor and manage the ventilator delivery of BSFTV by the ventilator, respiration sensors or sampling tubings can be attached or integrated into the heated circuit 27, the hose 28 or adaptor 70, all leading to the tracheal tube 60 and the patient 10 airway. Measurements could include internal pressure at the distal end of the device and the ventilator delivered gas temperature, humidity, flow or $F_IO_2$ or other gas properties (e.g., nitric oxide or helium concentration). Sensors from other devices that monitor pulse oximetry or tissue $CO_2$ can be attached in contact with skin or airway mucosal surface or similar body surfaces (such as the tissue interface of a tracheal stoma) and data transferred back to the ventilator device (wired or wireless transmission of various forms) either directly or through an intermediate device.

The present system's sensors in direct contact with the lumen, or indirect contact through gas sampling tubes attached to the lumen of tube 73 that allows a spontaneously-breathing patient to freely inhale and exhale in open exchange with the atmosphere can be used to measure or estimate the quantity and properties of the patient's breath. Sensors 75 in adaptor 70 can include but not be limited to thermistors, pressure or flow sensors. Wired or wireless transmission of various forms from sensors 75 can transfer data back to the ventilator device. Additionally, as illustrated in FIGS. 9, 11, 15, and 18, sampling tubes 77 in direct contact with the lumen of tube 73 that allows a spontaneously-breathing patient to freely inhale and exhale in open exchange with the atmosphere can transfer gas samplings back to sensors in the ventilator 20. As shown in FIG. 3, pressure transducer sensors 33, 34, $CO_2$ or other gas sensors 35 or additional sensors can be used to measure one or more physiologic or gaseous properties from the tubing sampling. When the purging pump 37 is disengaged by a valve or other mechanism, a valve assembly or similar device can additionally bypass the aspiration pump 36 and pressure within the gas sampling tube 30 can be in free communication with pressure transducers 33. The pressure differential can be used to determine flow using an additional transducer 34. The sampling tubing 30 can be used to draw sampled gas back into the device for measurement through use of an aspiration pump 36 or some similar mechanism with optional periodic purging of the line with air or a liquid (e.g., saline or water) using a positive pressure pump 37 or similar purging device. The aspiration pump 36 would deliver the sample to sensor/measurement devices within the present device. Examples of sensor/measuring devices include a helium, nitric oxide, oxygen or $CO_2$ analyzer 35.

Data generated by sensors at or near adapter 70 and data generated by sensors within the ventilator 20 from samples collected at or near adapter 70 and data generated from any other sensors, such as an oxygen or other gas analyzer 29, pressure transducer 23 and flow transducer 24 incorporated into the gas delivery mechanism of the ventilator 20 are electronically transferred to the processor 21 through analog-to-digital conversion as needed, so digital information either reaches the processor or is converted from analog to digital at the processor 21. The processor 21 is typically in bidirectional or two-way communications with the entire sensing/measurement system (including sensors, aspiration and purging systems). The processor 21 also governs any necessary valve control, visual or audio alarms, output regulation, calibration, quality control or operation status and self-test or auto-regulation information. In particular, at least one of the sensors measures a physical property (e.g., pressure, temperature, flow or carbon dioxide level) associated the patient's respiratory cycle. It should be understood that the processor 21 can be a microprocessor, controller or any other suitable type of hardware with sufficient intelligence to monitor the sensors, detect a desired phase (or phase component) of the patient's respiratory cycle, and control the ventilation system to deliver a predetermined flow profile of oxygen-containing gas varying over each inspiratory and expiratory phase of the respiratory cycle.

As another embodiment of the invention, one or more of the sensor/measurement devices, aspiration and purging systems and related hardware/software can be external and removably attached to the present device with appropriate ports 38 and 39 to connect the device to communicate with the processor 21, sensor/measurement devices and sampling tubing located on or adjacent to adaptor 70. Furthermore, devices in communication with the present device could include monitors such as pulse oximeters and tissue $CO_2$ monitors. In addition to sensor/measurement devices at or adjacent to adaptor 70 or other sensor/measurement devices can be integrated within the delivery system of the present device.

The processor 21 is also in two-way or bidirectional communication with a local and optional remote graphic user interface 40 (GUI) or similar device with control panel, and with a local or optional remote audio alarm system 42. The GUI display 40 allows the user to set flow-targeted parameters, including peak flow, or any of the instantaneous flow waveform characteristics that can be targeted for a respiratory phase or component of a respiratory phase. Respiratory phases include an inspiratory phase, a transition phase from inspiratory to expiratory, an expiratory phase, and a transition phase from expiratory to inspiratory. Additionally, there are components to both the inspiratory and expiratory phases. In one embodiment, those flow-targeted peak flows (e.g., inspiratory and expiratory or optional peak transition flows) and relative flow waveform examples of described flows targeted to phases or components of the phases can be graphically presented to the user as options (among other flow pattern options) for selection. Selected "Help" screens could walk the user through various decision trees, such as selection of phase-related peak flows and flow patterns based upon specific management goals. The operator GUI 40 or other control interface allows the user to assess, measure, monitor, adjust or alter any parameter chosen by the user. The primary targeted parameter is peak flow and the associated flow pattern. However, the user can adjust for secondary parameters including, but not limited to delivered gas oxygen concentration, as well as the concentration of other medical gases such as air, helium, or nitric oxide, and the delivered temperature and humidity.

Though the system is flow targeted, every ventilation system must have secondary, or fail safe back-ups. As with other ventilation systems, excessive internal pressures within the present device or within the flow delivery circuit can be measured. Similarly, sensors, measuring devices and/or gas sampling tubing attached to, or associated with the adaptor 70 attached to the airway interface device 60 can integrate with the present system to sense over-pressurization within the patient airway. The GUI interface 40 can allow the user to select default or custom pressure limits, and pressure exceeding that limit at any point will be dissipated (e.g., through the pressure relief valve noted in FIG. 3) with the appropriate audible alarm 42 and visual alarm. The intelligent processor 21 can utilize data from all valves, sensors, measurement devices or other systems integrated within or in communication with the present device to perform calibration, quality assurance checks, other automatic tests or evaluations and to make automatic adjustments and compile reports.

The processor 21 can use data from the sensors, measurement devices or sampling tubing related to the adaptor 70 attached to the patient airway interface devices 60 to determine the phases and components of phases of the respiratory cycle of the self-breathing patient 10. Examples include, but are not limited to, flow (e.g., direct flow measurement, thermistor or differential pressure assessment), airway pressure and airway $CO_2$ waveform analysis. The processor 21 can then utilize this data for ventilator delivery of breath-synchronized flow-targeted ventilation and monitoring.

Airway $CO_2$ waveform analysis, especially as utilized with tracheal tubes, tracheal tube inner cannulas and tracheal catheters, can be derived from gas obtained near the carina, thus eliminating a substantial portion of anatomic dead space. Additionally, end-tidal $CO_2$ analysis can eliminate some of the physiologic dead space from wasted alveolar ventilation a known confounding factor in end-tidal capnography accuracy. This gas sampling method more closely reflects alveolar partial pressure of $CO_2$, which is similar to arterial partial pressure of $CO_2$, the determinant of adequacy of ventilation. The real time breath-by-breath end-tidal $CO_2$ analysis and trending through processor 21 will reflect the adequacy of ventilation in the self-breathing patient 10 supported by the present invention. Accuracy of end-tidal capnography may be enhanced by the invention if the sample tubing opening is positioned at the distal end of the open lumen of adapter 70 near the carina and processor 21 interrupts mixing tracheal gas from ventilator flow for a very brief period during the transition between end of expiratory flow and beginning of inspiratory flow, where there is normally no flow during self-breathing.

Utilizing devices sensing qualitative breathing data from a thermistor, data indirectly assessing flow from pressure changes during breathing, or directly measuring the $CO_2$ waveform, the processor 21 can deliver the ventilator flow-targeted waveform synchronized to the phases and components of phases of the respiratory cycle of the self-breathing patient 10. However, exact measurement confirmation of flow and volume contributed by the present invention would be clinically useful. The processor 21 can utilize flow sensors 23 to calculate the flow delivered by the ventilator during the time of inspiratory phase ($T_I$) and expiratory phase ($T_E$). Processor 21 can document characteristics of the flow waveform and also integrate flow into the volume delivered by the ventilator during inspiration and expiration.

When the cuff of the tracheal tube remains inflated, the self-breathing inspired flow can be obtained utilizing direct flow measurement through flow sensor 75 or differential pressure measurements from sample tubings 77 in contact with the open self-breathing lumen within the tracheal tube created by adaptor 70. The processor 21 can identify the self-breathed flow measured by the sensor during inspiration ($T_I$), and calculate the flow waveform and integrate inspiratory flow over ($T_I$) to yield self-inspired volume. When both the inspiratory flow waveform properties and volume delivered during inspiration by the patient's self-breathing and ventilator delivery have been calculated by processor 21, the summation of the two waveforms and inspired volumes by processor 21 yields the complete flow waveform and total inspired volume delivered to the patient.

Similarly, the processor can estimate the expiratory gas volume sensed through the open self-breathing lumen of adaptor 70 by flow data obtained during the time of expiration ($T_E$). The processor 21 can calculate the expired volume by integration of the flow over $T_E$.

Various processor calculations of physiologic parameters can be presented to the user through the GUI 40 to indicate the respiratory-cardio physiologic status of the patient 10. Acceptable ranges can be set by the user, with GUI 40 and audio alarms 42 set to alert exceptions. With an intelligent processor 21, device-monitoring information and physiologic data can input into a servo-feedback loop that allows the present invention to make clinician-defined, rules-based adjustments in properties, such as adjustments of the clinician's initially selected waveform delivery using monitoring and physiologic data criteria to achieve the clinician's desired patient outcome. The user can set appropriate limits with an appropriate local or remote GUI 40, and limits for audible alerts and alarms 42.

Adaptor.

Embodiments of the adaptor 70 for use with a conventional tracheal tube (e.g., a tracheostomy tube 80 or endotracheal tube 90) are illustrated in FIGS. 4-19. IN BSFTV mode, an adaptor 70 is used to removably secure an inner catheter 73 within the patient's tracheal tube, while still allowing unrestricted spontaneous inspiratory and expiratory breathing through the tracheal tube and a port in the adaptor 70. The adaptor 70 has a cap or housing with a first cylindrical connector 71 that removably fits into and engages the standard connector on a ventilator hose, and a second cylindrical connector 72 that removably fits over and engages the standard proximal connector on a tracheal tube 80, 90. An inner cannula 73 can be removably inserted through the proximal opening of the tracheal tube to effectively divide the tracheal tube into two lumens. In BSFTV mode, one lumen is used for supplying oxygen-containing gas from the ventilator to the patient, while the second lumen allows spontaneously-breathing patient to freely inhale and exhale in open exchange with the atmosphere. FIG. 4 is a vertical cross-sectional view of the adaptor 70 by itself.

Figure 5:
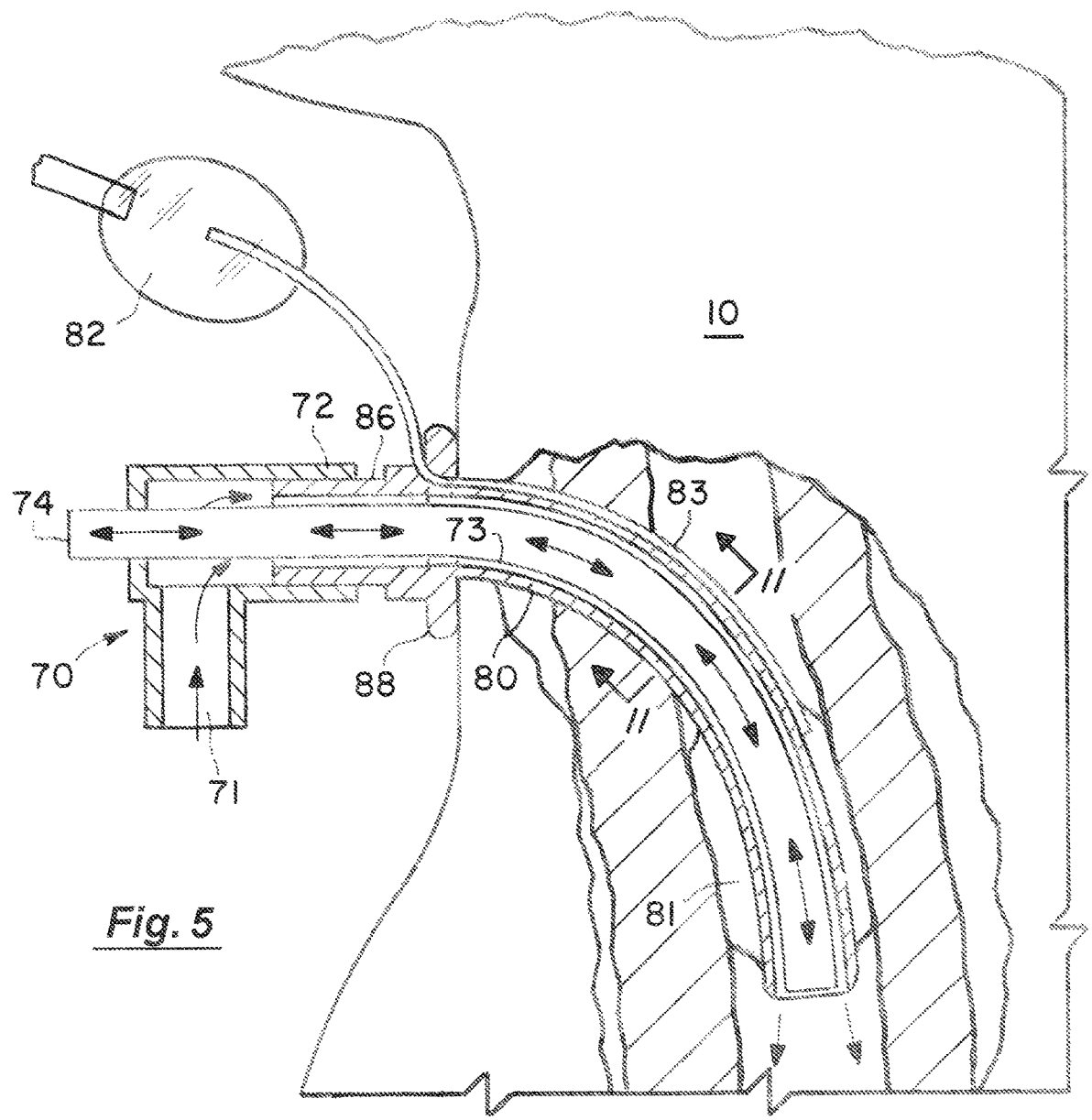
FIG. 5 is a vertical cross-sectional view of the assembly of the adapter 70 and a tracheostomy tube 80 after insertion into a patient's airway.
Figure 6:
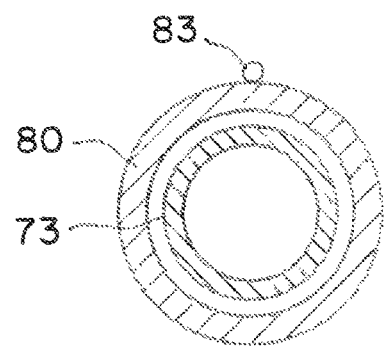
FIG. 6 is a cross-sectional view of the cannula 73 of the adaptor 70 and the tracheostomy tube 80.

For example, a standard cuffed tracheostomy tube 80 (FIG. 1) utilized for CSPPV can be used to convert to BSFTV with an open system. FIGS. 5-9 provide detail concerning an embodiment of adaptor 70 used in conjunction with a conventional tracheostomy tube 80. In this embodiment, the inner cannula 73 of the adaptor 70 shown in FIG. 4 can be inserted into a standard tracheostomy tube 80 with inflatable cuff 81. The inner cannula 73 can be made of flexible plastic material that is curved to approximate the contour of a tracheostomy tube 80. When the inner cannula 73 is fully inserted, the cross-sectional view in FIG. 6 shows that the diameter of the outer wall of the inner cannula 73 is less than the inner diameter of the tracheostomy tube 80, creating an annular second lumen for supplying a flow of oxygen-containing gas to the patient. The cross-sectional view in FIG. 5 illustrates that the annular lumen between the outer wall of the inner cannula 73 and inner diameter of the tracheostomy tube 80 is maintained along the longitudinal axis from the proximal opening to the distal opening of the tracheostomy tube 80. The open proximal end 74 of the inner cannula 73 extends through the cap of the adapter 70 to provide a port to the atmosphere for patient inhalation and exhalation.

The adapter 70 includes a cylindrical connector 72 with an inner diameter that snugly, but removably attaches to a standard 15 mm connector 86 on the proximal end of the tracheostomy tube 80. The adapter 70 can rotate circumferentially around the 15 mm tracheostomy connector 86. Another cylindrical connector 71 extends at, for example, a 90 degree angle to the adapter 70, for removable attachment to a ventilator hose 28. This connector 71 is in fluid connection with the inner cavity of the adapter 70, so that gas delivered by the ventilator flows through adaptor 70 and the annular lumen within the tracheostomy tube 80 to the patient 10. The connector 71 has an inner diameter designed to fit inside a standard ventilator hose 28 through its integrated connector. The cap of the adaptor 70 has a flexible air-tight seal that maintains the position of the inner cannula 73, but allows rotation of the adaptor 70 around the tracheostomy tube connector 86 to orient the ventilator tubing connector 71 and ventilator hose 28 to an adjustable position in relationship to the patient's head and position of the ventilator 20 with relation to the patient's bedside.

The proper insertion of the inner cannula 73 and connection to the ventilator hose 28 allows the flow-targeted waveform to be delivered through the annular lumen between the inner cannula 73 and tracheostomy tube 80, and dispersed into the trachea during the patient's breathing cycle. The inner cannula 73, which is in open communication between the trachea and atmosphere, allows simultaneous unrestricted self-breathing by the patient.

Figure 7:
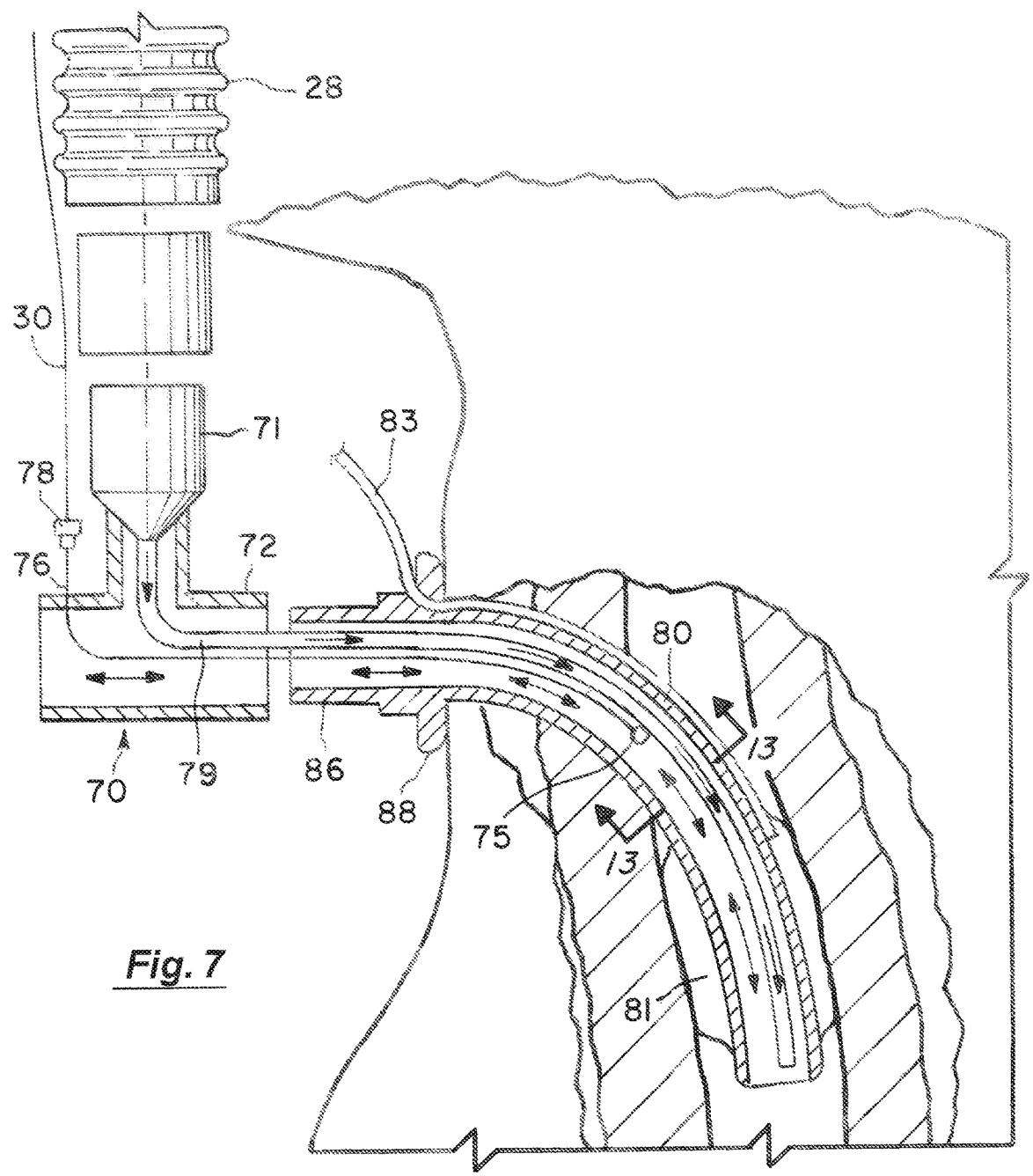
FIG. 7 is a vertical cross-sectional view of an alternative embodiment of the adaptor 70 with a smaller-diameter catheter 79 extending along the tracheostomy tube 80 after insertion into the patient's airway. A respiration sensor 75 is attached to the exterior of the catheter 79 and connected by wire to the ventilator.
Figure 8:
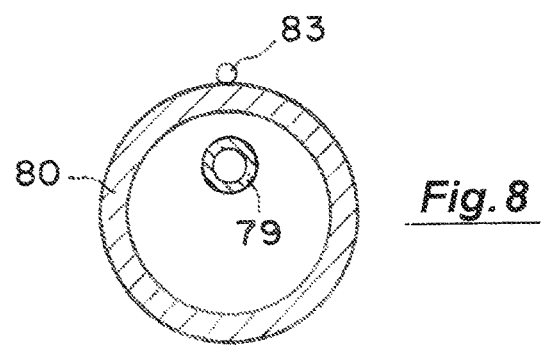
FIG. 8 is a cross-sectional view of the catheter 79 of the adaptor 70 and the tracheostomy tube 80.
Figure 9:
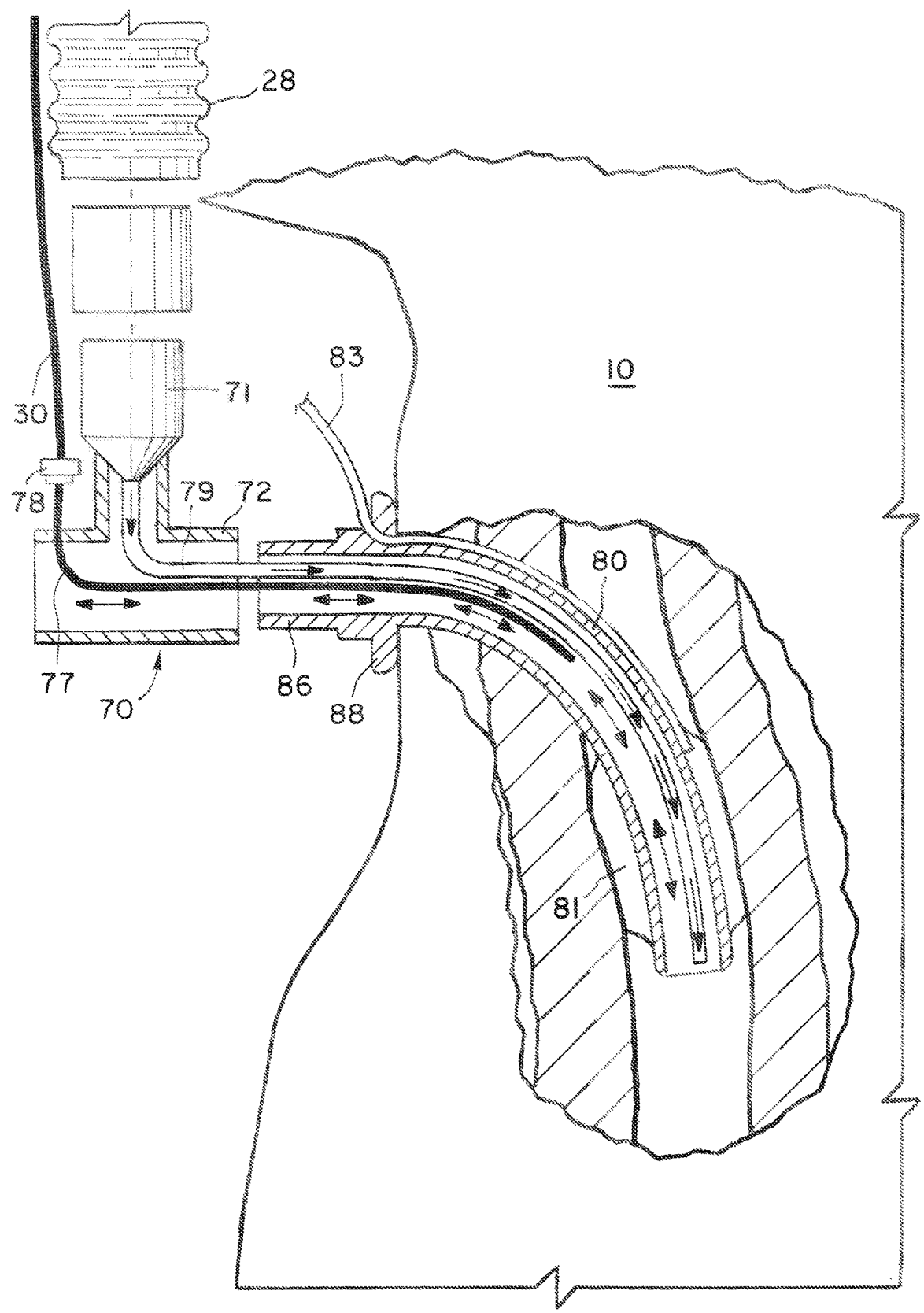
FIG. 9 is a vertical cross-sectional view of an embodiment of the present invention similar to FIG. 7, but with a gas sampling tube 77 in place of the respiration sensor.

In an alternative embodiment, a smaller-diameter catheter 79 shown in FIGS. 7-9 may be inserted through the tracheostomy tube 80. For the purposes of this disclosure, the term "cannula" should be broadly construed as either an inner cannula 73 as shown in FIGS. 4-6, or a smaller-diameter catheter 79 as shown for example in FIGS. 7-9. These terms should be considered to be interchangeable.

Returning to the embodiments in FIGS. 7-9, the smaller diameter catheter 79 extends from the cap of the adaptor 70 and is inserted into a proximal opening of a standard tracheostomy tube 80, as shown in FIG. 7. The diameter of the catheter 79 can be about the same or larger than a conventional transtracheal catheter depending upon gas delivery needs. The cross-sectional view in FIG. 8 illustrates that the outer diameter of the catheter 79 is substantially less than the inner diameter of the tracheostomy tube 80, thereby creating a space allowing unrestricted self-breathing through the tracheostomy tube lumen. The cross-sectional view in FIG. 9 illustrates that the space between the outer wall of the catheter 79 and inner diameter of the tracheostomy tube 80 is maintained along the longitudinal axis from the proximal opening to the distal opening of the tracheostomy tube.

Figure 12:
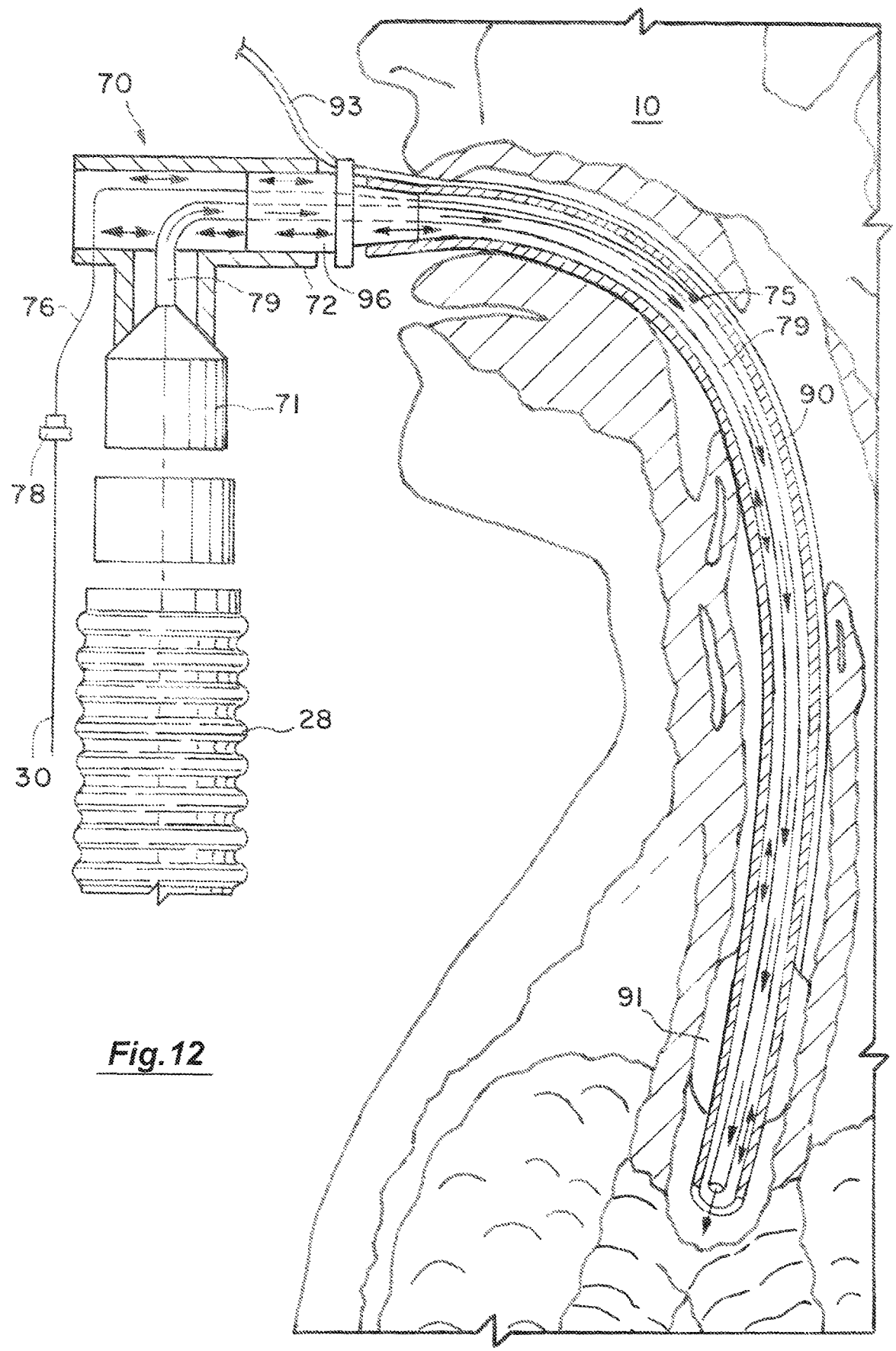
FIG. 12 is a vertical cross-sectional view of an embodiment of the present invention with a smaller-diameter catheter 79 extending along an endotracheal tube 90 after insertion in the patient's airway.
Figure 13:
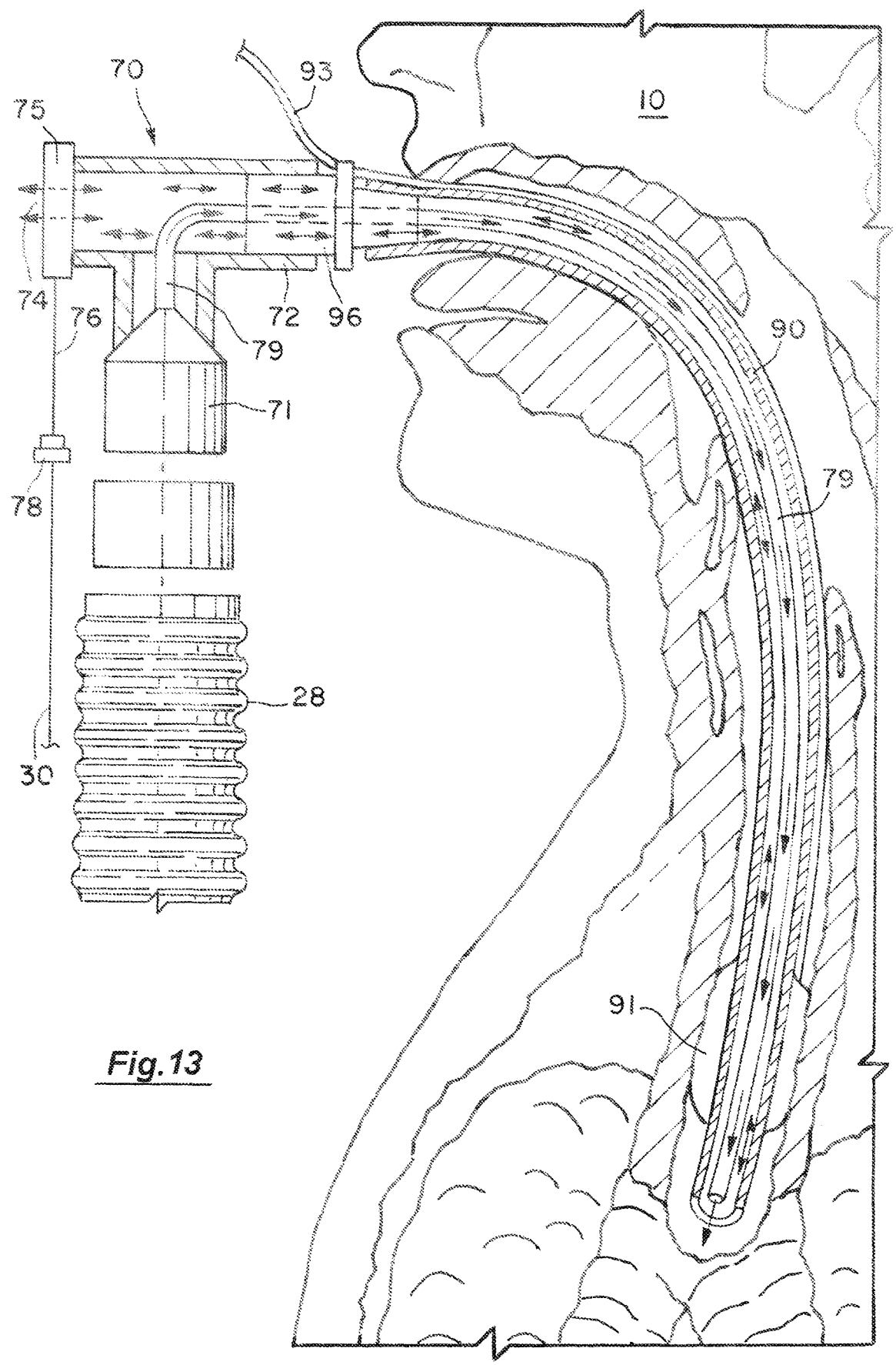
FIG. 13 is a vertical cross-sectional view of an embodiment of the present invention similar to FIGS. 17 and 18, with a flow sensor 75 at the proximal opening 74 of the adaptor 70.

The configuration of the adaptor 70 in these embodiments is also somewhat different. Here again, the adaptor 70 includes a cylindrical connector 72 that removably fits over and engages the standard 15 mm connector 86 on the proximal end of the tracheostomy tube 80. The assembly can rotate circumferentially around the 15 mm tracheostomy connector 86. The adaptor 70 also has another cylindrical opening 71 that removably fits into the standard connector on a ventilator hose 28, as previously discussed. However, the proximal end of adaptor cap is open, as shown in FIG. 7, to define a port so that the patient can freely breathe in and out through the open lumen of the tracheostomy tube 80 surrounding the catheter 79. The transtracheal catheter 79 has an elbow which is bonded to the conical segment 71 of adaptor 70, which in turn reversibly connects to the cylindrical connector of ventilator hose 28 as shown in FIGS. 7, 9, and 12-16. As before, one or more respiration sensors 75 can be placed within or attached to the outer wall of the catheter 79 to detect and monitor the patient's self-breathing. FIGS. 7 and 12 illustrate a sensor 75, such as a thermistor with a wired connection 76 exiting from the cylindrical extension above the attachment of the catheter elbow to the conical segment. The communication of the sensor 75 with the ventilator 20 may be wired or wireless. Alternatively, the sensors may be external to the ventilator, but in communication with processor 21.

Figure 15:
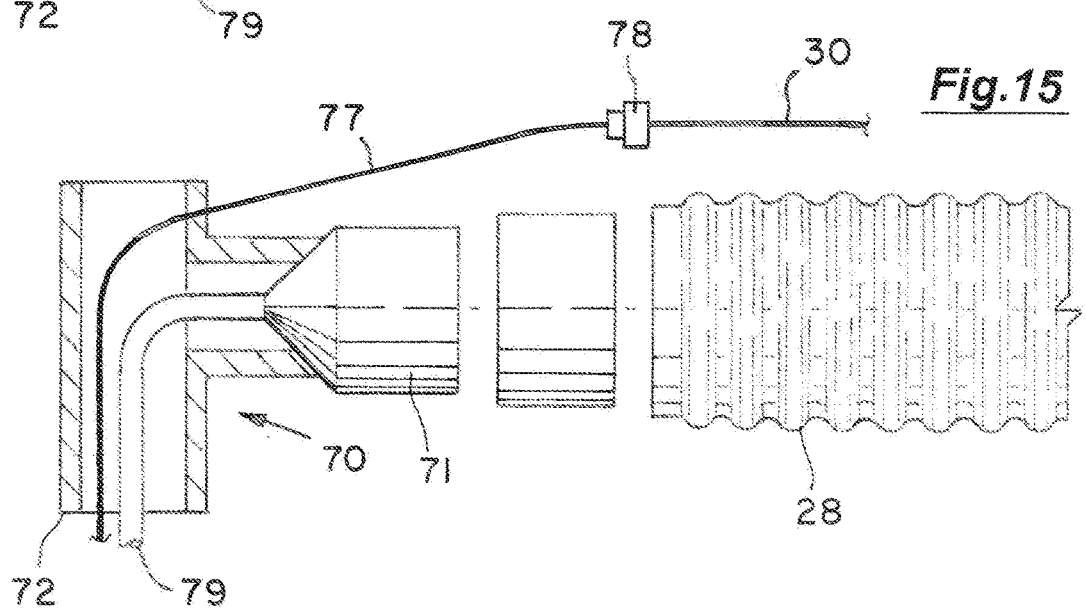
Figure 14:
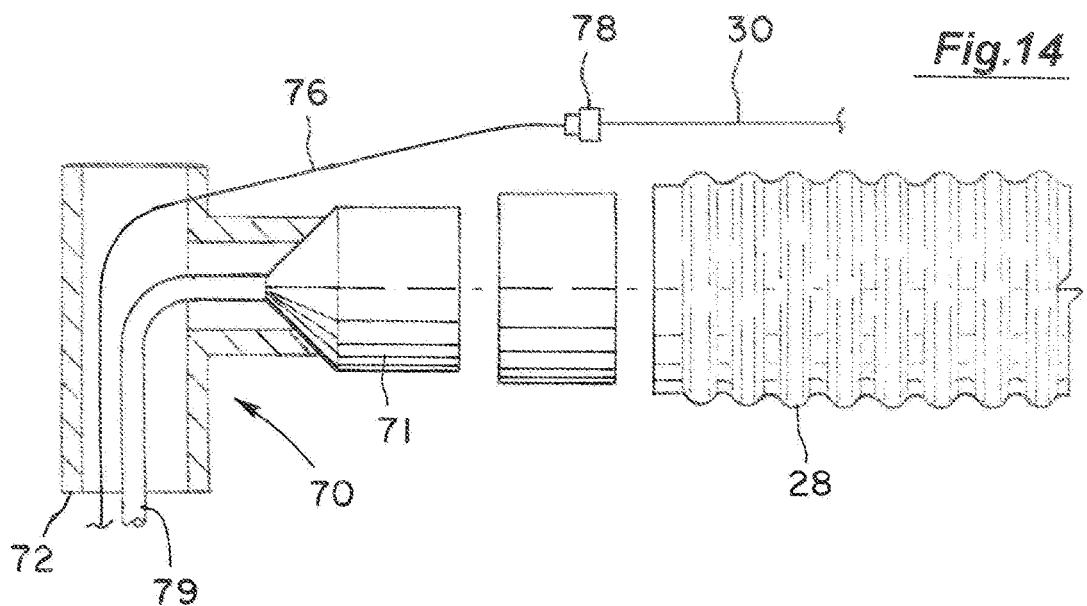

As shown in FIGS. 9 and 15, one or more sampling tubings 77 can be placed within and along the outer wall of the catheter 79 with the distal opening at one or more positions along the outer catheter wall and in fluid connection with the lumen of the tracheostomy tube to detect and monitor the patient's self-breathing. As noted previously, the tubing can allow a sensor in the ventilator 20 to measure pressure within the lumen of the tracheostomy tube or sample gas that is delivered to the sensor within the ventilator 20. The aspirating pump 36 and purging pump 37 systems can be utilized for gas sampling, as previously disclosed. Alternatively, the sensors may be external to the ventilator, but in communication with processor 21. FIGS. 9 and 15 illustrate the tubing exiting the adaptor 70 through the cylindrical extension above the point of connection of the catheter 79 to the conical ventilator tubing connector 71. An air-tight connection 78 facilitates attachment of the tubing 77 to the tubing 30 affixed to the ventilator tubing 28.

Figure 16:
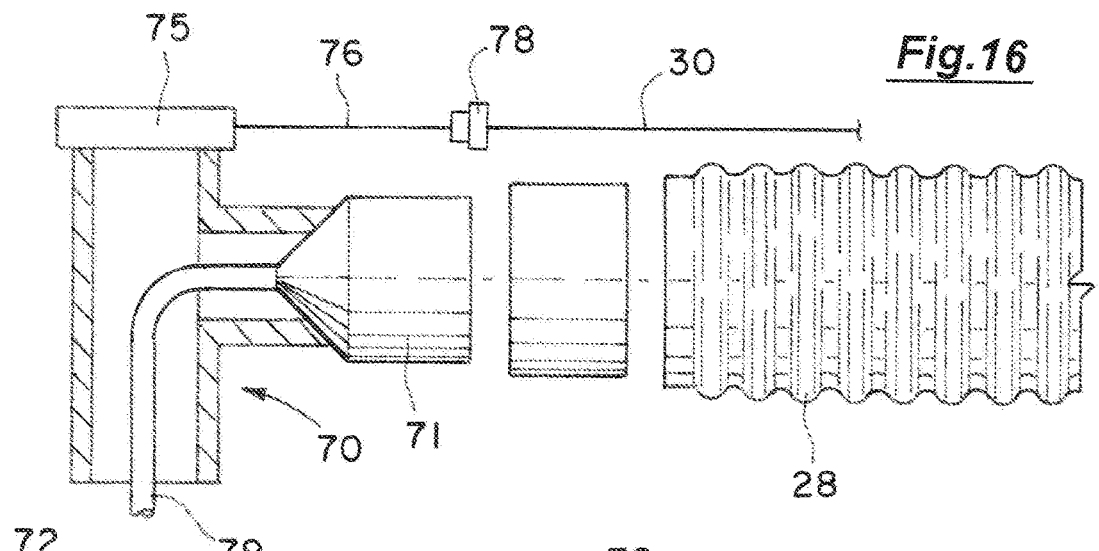
FIGS. 14-16 are cross-sectional views of three embodiments of an adaptor 70 with a smaller diameter catheter 79 showing different configurations of the sensor wire 76 or sampling tube 77 that can be used for monitoring patient respiration.

In another embodiment, a flow sensor 75 shown in FIG. 16 can be attached to the proximal (top) opening of the adaptor 70 to allow measurement of flow during patient self-breathing to detect and monitor the patient's self-breathing. FIG. 16 depicts a wired connection 76 exiting from the flow sensor 75 and attaching via connector 78 to a wire 30 affixed to the ventilator tubing 28, transmitting information to the ventilator processor 21 either directly or through an external device.

It should be noted that the adaptor 70 may either deliver flow through the annular lumen defined between the outer wall of the inner cannula 73 and the inner wall of the tracheostomy tube 80, or through the inner cannula 73. In the specific embodiment in FIGS. 4-6, the patient's self-breathing occurs through the lumen of the inner cannula 73. A fenestrated tracheostomy tube is not necessary because adequate self-breathing occurs through the inner cannula 73. In contrast, in the embodiments shown in FIGS. 7-9, flow is delivered via the inner cannula 79, and self-breathing occurs via the annular lumen between the tracheostomy tube 80 and the inner cannula 79. Similarly, a fenestrated tube is not necessary.

Figures 1, 2:
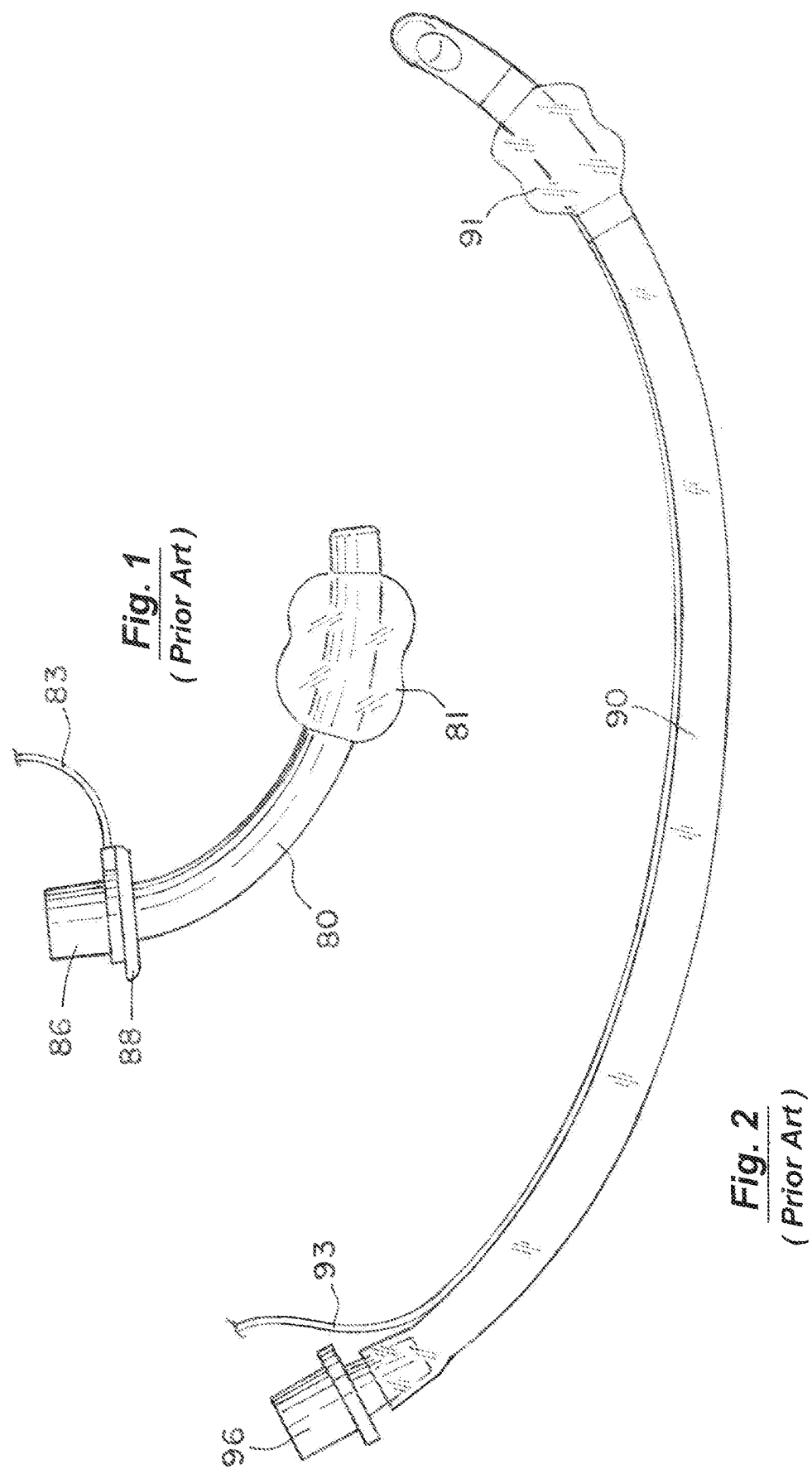
FIG. 1 is a side view of a conventional tracheostomy tube 80.
FIG. 2 is a side view of a conventional endotracheal tube 90.

Also note that the tracheal tube remains in place in the patient's airway throughout this process, and the cuff 81 or 91 can be inflated using inflation tube 83 or 93 of the tracheal tubes illustrated in FIGS. 1-2 and any degree of inflation can be monitored by test balloon 82 illustrated in FIG. 5. As an option, the cuff 81 or 91 may be partially or completely deflated to prevent contaminated upper airway secretions from pooling above the cuff and also allow for some additional self-breathing around the tracheal tube and through the upper airway, if needed. Partial or complete deflation of a tracheostomy tube cuff 81 allows some gas to pass up through the vocal cords to facilitate speech.

Figure 10:
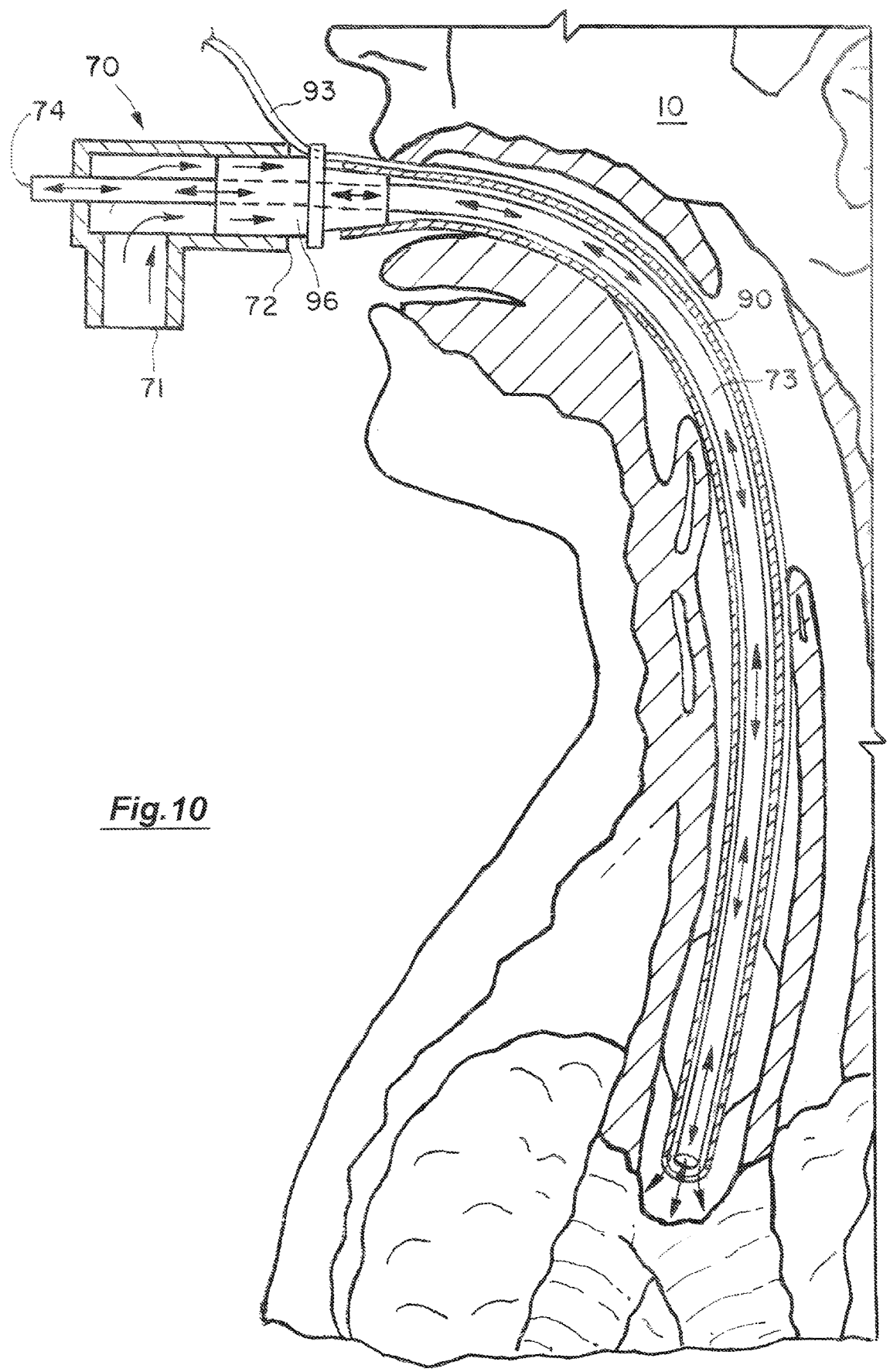
FIG. 10 is a vertical cross-sectional view of the adapter 70 and an endotracheal tube 90 after insertion into a patient's airway.

FIGS. 10-13 show additional embodiments of the present invention using an adaptor 70 in conjunction with a conventional endotracheal tube 90. Similar to the previous embodiments in FIGS. 4-6, the inner cannula 73 of the adaptor 70 can be inserted into a standard endotracheal tube 90 with an inflatable cuff 91. When the inner cannula 73 of the adaptor 70 is fully inserted, the diameter of the outer wall of the inner cannula 73 is less than the inner diameter of the endotracheal tube 90, creating an annular region allowing unrestricted self-breathing through the endotracheal tube lumen. The cross-sectional view in FIG. 10 illustrates that the annular region between the outer wall of the inner cannula 73 and the inner diameter of the endotracheal tube 90 is maintained along the longitudinal axis from the proximal opening to the distal opening of the endotracheal tube 90. Here again, the adaptor 70 has a connector 72 with an inner diameter that snugly, but removably attaches to a standard 15 mm connector 96 on the proximal end of the endotracheal tube 90.

Figure 11:
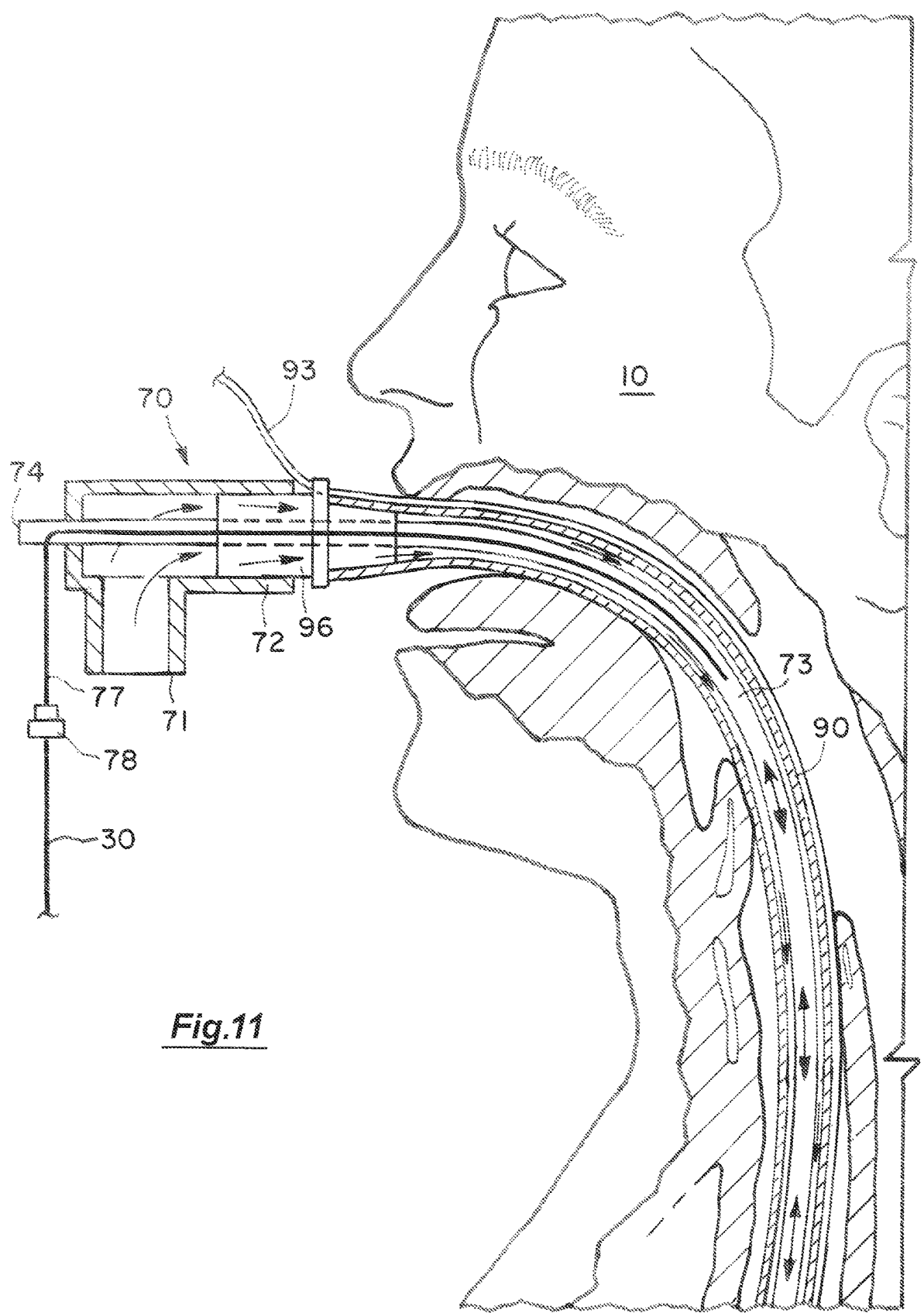
FIG. 11 is a vertical cross-sectional view of an embodiment of the present invention similar to FIG. 10 with a gas sampling tube 77 extending along the interior of the cannula 73.
Figure 19:
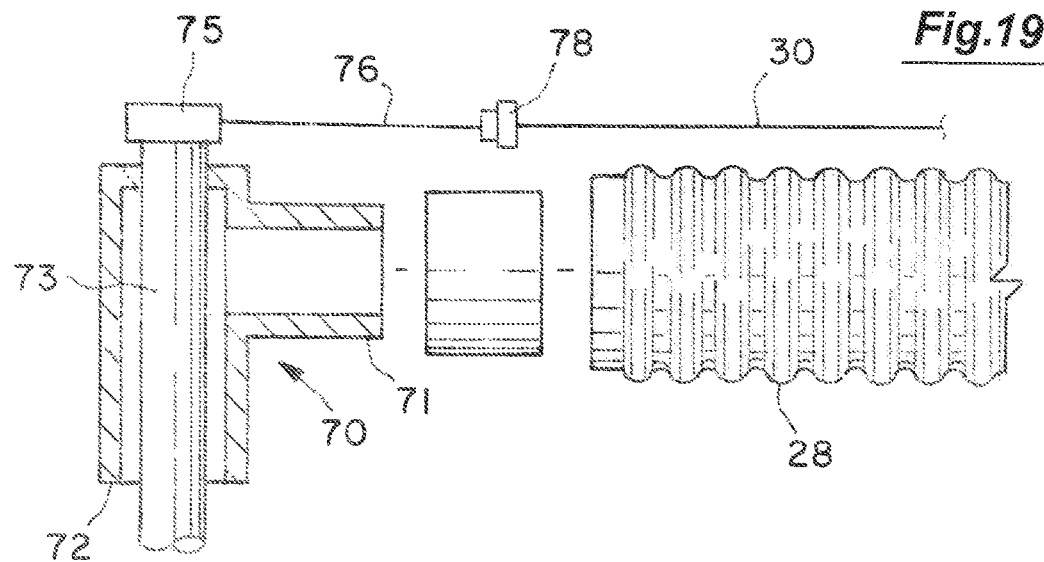
FIGS. 17-19 are cross-sectional views of three embodiments of an adaptor 70 with an inner cannula 73 showing different configurations of the sensor wire 76 or sampling tube 77 that can be used for monitoring patient respiration.
Figure 18:
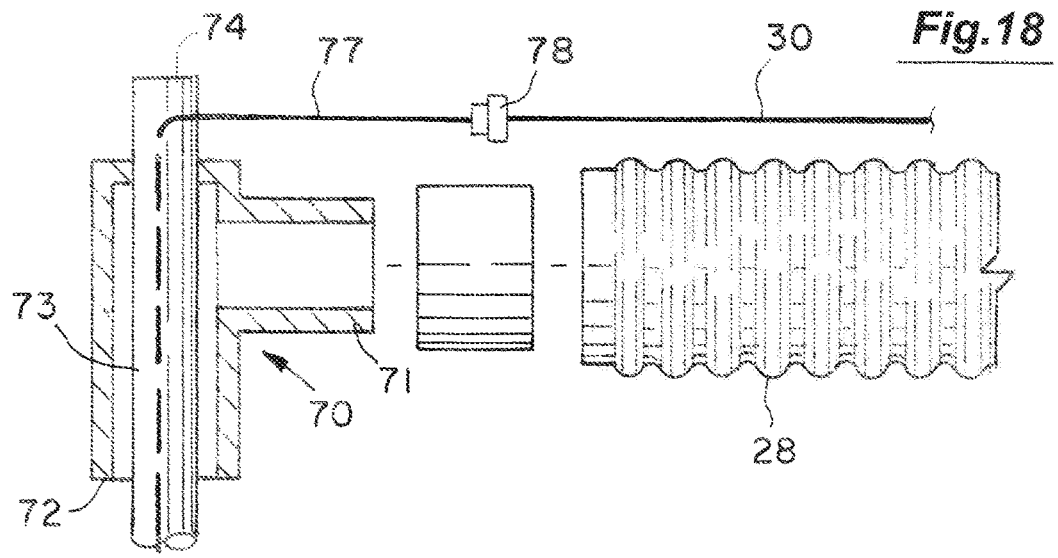
Figure 17:
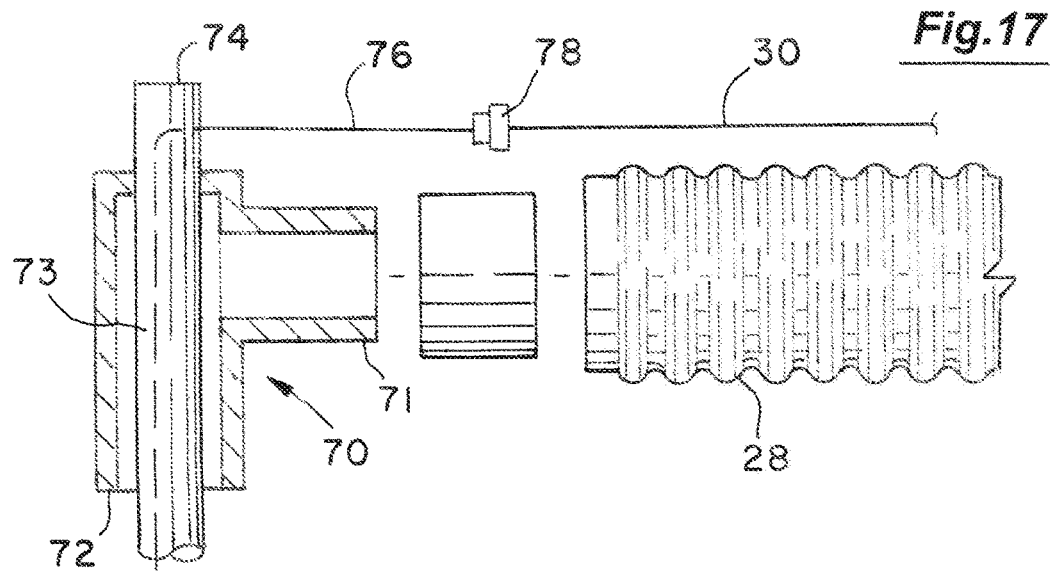

To detect and monitor the patient's self-breathing, respiration sensors can be placed within or attached to the inner wall of the inner cannula 73. (FIG. 4). The sensor 75 such as a thermistor or pressure sensor may be in communication through attachment to wire 76 with connector 78 used for connectivity to wire 30 attached to the ventilator hose as shown in FIG. 17. Transmission to the ventilator may be wired or wireless, and may be routed through a separate device. Alternatively, one or more sampling tubings 77 can be placed within the inner wall of the inner cannula 73 (FIGS. 11 and 18). In another embodiment to detect and monitor the patient's self-breathing, a flow sensor 75 shown in FIG. 19 can be attached to the proximal (top) opening of the adaptor 70 to allow measurement of flow during patient self-breathing. Data transmission to the ventilator may be wired as shown in FIG. 19 or wireless, and may also be either direct or routed through a separate device.

Examples of Use

Figure 20:
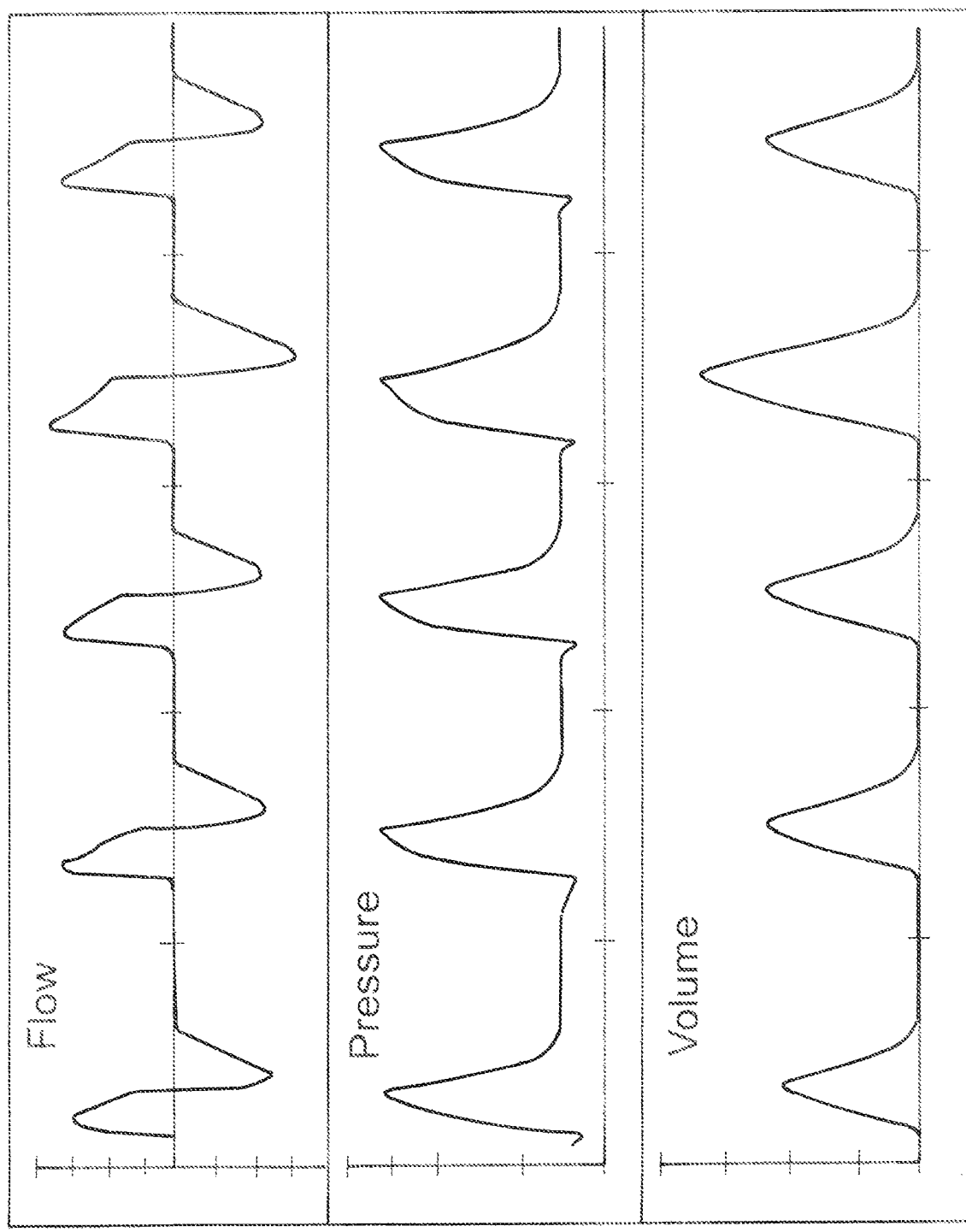
FIG. 20 is a set of graphs illustrating the respiratory mechanics with a prior art pressure-targeted CSPPV.

FIG. 20 illustrates pressure, flow and volume waveforms with breathing cycles experienced by a patient receiving prior art pressure-targeted CSPPV. Time is on the horizontal axis. There are four phases to the respiratory cycle. There is a transition phase between expiration and inspiration, which is followed by the inspiratory phase. Similarly, there is a transition phase between inspiration and expiration which is followed by the expiratory phase. The inspiratory and expiratory phases also have different components. Prior art pressure-targeted CSPPV systems are designed to take over the patient's normal spontaneous negative pressure self-breathing. For example in FIG. 20, this patient is receiving a commonly prescribed targeted pressure of 5 cm H2O during end expiration, or positive end-expiratory pressure (PEEP). During the beginning of the inspiratory phase, the patient makes an effort to spontaneously negative pressure breathe, which results in a transient drop in the applied positive pressure to approximately 3 cm H2O, but not to a normal negative value. A series of pressure-targeted breaths are triggered each time the patient attempts to normally breathe, and the positive pressure ventilator will override the patient's natural efforts and will force, or pressurize the breath to exactly achieve the targeted maximal inspiratory pressure of 25 cm H2O. Once the targeted pressure is reached, the exhalation valve opens and allows pressure to drop on exhalation, but the valve then closes when the targeted expiratory pressure of 5 cm H2O is reached. On a breath-by-breath basis, the maximum inspiratory flow and flow delivery patterns vary. A breath with a longer inspiratory time alters flow delivery and achieved tidal volume, even though targeted pressure is unchanged. Similarly, the maximum expiratory flows and flow patterns vary even though a targeted PEEP is achieved and maintained. Peak inspiratory flows and flow patterns are relatively independent of the target inspiratory pressure. Peak expiratory flows and flow patterns are relatively independent of the target expiratory pressure.

Figure 21:
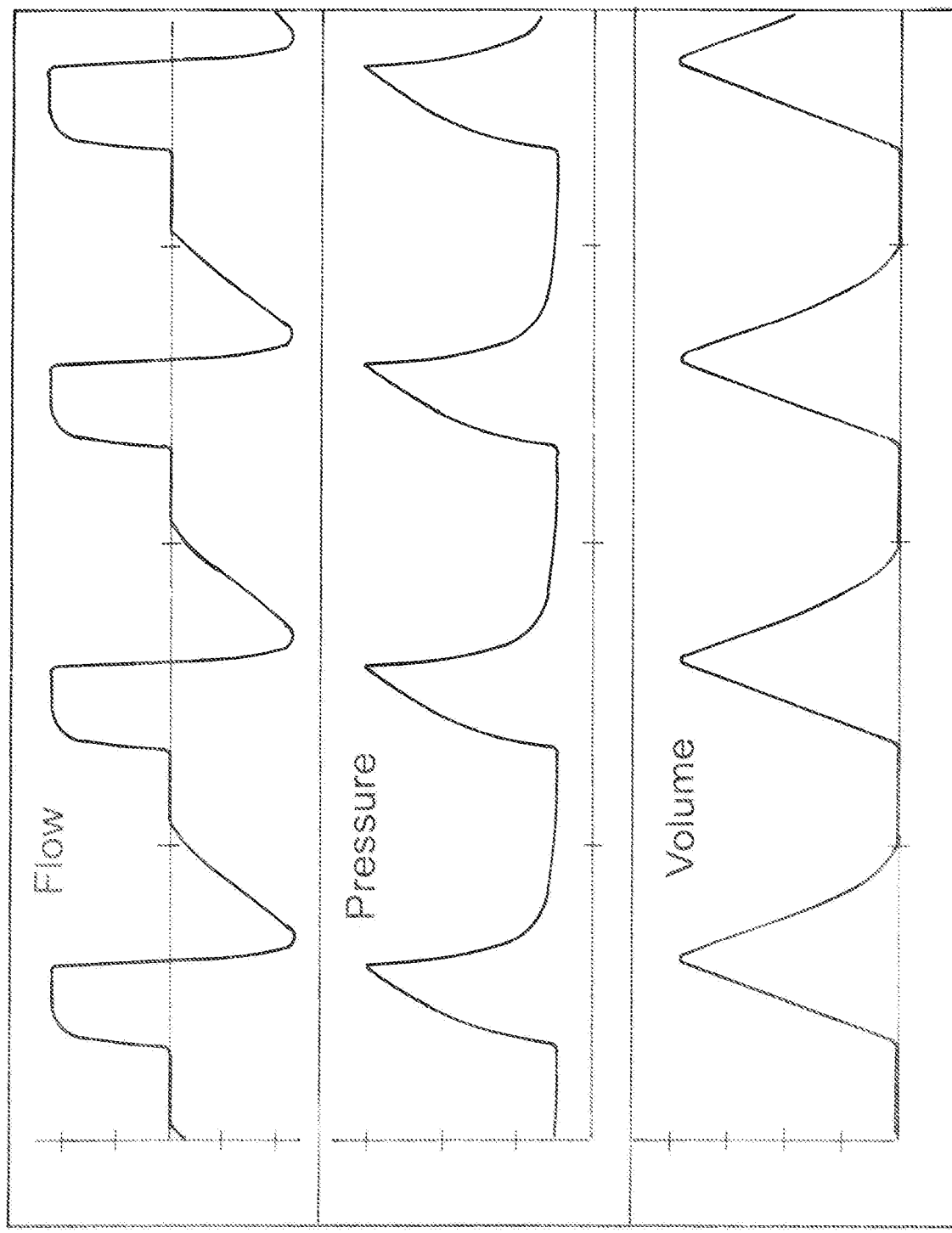
FIG. 21 is a set of graphs illustrating the respiratory mechanics with prior art volume-targeted CSPPV.

FIG. 21 illustrates implementation of a prior art volume-targeted CSPPV. The ventilator has a targeted tidal volume of 800 ml which is achieved with each breath. With a closed system and the mechanical properties of this patient's lungs (resistance, compliance, etc.) delivery of the targeted volume results in generation of 30 cm H2O at peak inspiration, and the pressure dissipates only when the exhalation valve opens allowing the patient to exhale. In addition to the targeted inspired volume, there is a commonly used expiratory targeted pressure, which is 5 cm H2O of PEEP that is maintained by closure of the expiratory valve. The patient is not making any efforts to self-breathe, and negative pressure deflections below the PEEP level are not seen. Consequently, because of the closed system and absence of self-breathing, the targeted volume is achieved with each breath and no variations in pressure, flow or flow patterns are seen in this steady state. Had self-breathing efforts occurred with volume-targeted CSPPV, variability in peak pressure and both peak flow and flow patterns would have been observed.

Figure 22:
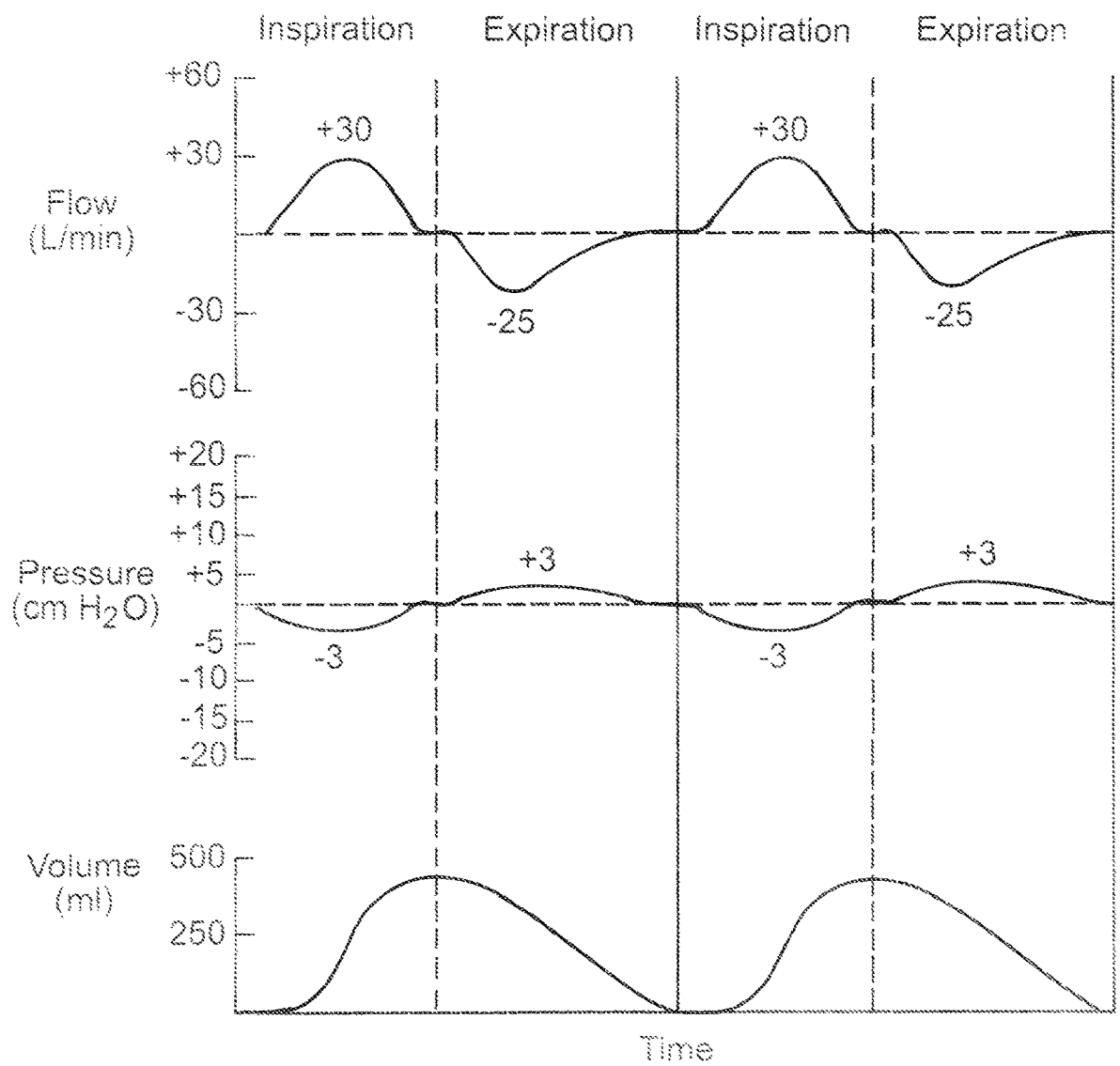
FIG. 22 is a set of graphs illustrating the respiratory mechanics in a normal healthy person in a relaxed state.

FIG. 22 illustrates respiratory mechanics in a normal negative-pressure self-breathing healthy person in a relaxed state. This is representative of how individuals spontaneously breathe when independent from either a positive pressure or negative pressure mechanical ventilator. In short, individuals self-generate a negative or sub-atmospheric pressure that draws the breath into the lungs. During the inspiratory phase, the person uses respiratory muscles to generate negative pressure. Since the lungs are healthy, minimal work of breathing (WOB) is required to draw adequate flow into the lungs. At about mid-inspiration the amount of negative pressure as well as flow into the lungs has reached the peak, and values begin to return to the baseline of zero pressure and flow (sinusoidal pattern). During the transition phase between inspiration and expiration there is a slight pause where negative pressure has dissipated, inspiratory flow has ceased and no additional volume has entered the lungs. During the exhalation phase, the elastic recoil of the lungs and chest wall is enough to cause the gas flow to carry the inspired volume out of the lungs and into the atmosphere under negligible resistance. Minimal positive pressure is generated and little or no expiratory WOB is done. Again, expiratory pressure and flow occur in a sinusoidal pattern. There is also a brief period of zero pressure and zero flow in the transition phase between expiration and inspiration where no volume exchange occurs. The ratio of inspiration to expiration is approximately 1:1.5, which is an efficient pattern that maintains a normal respiratory rate and adequate time for exhalation with normal lungs.

Figure 23:
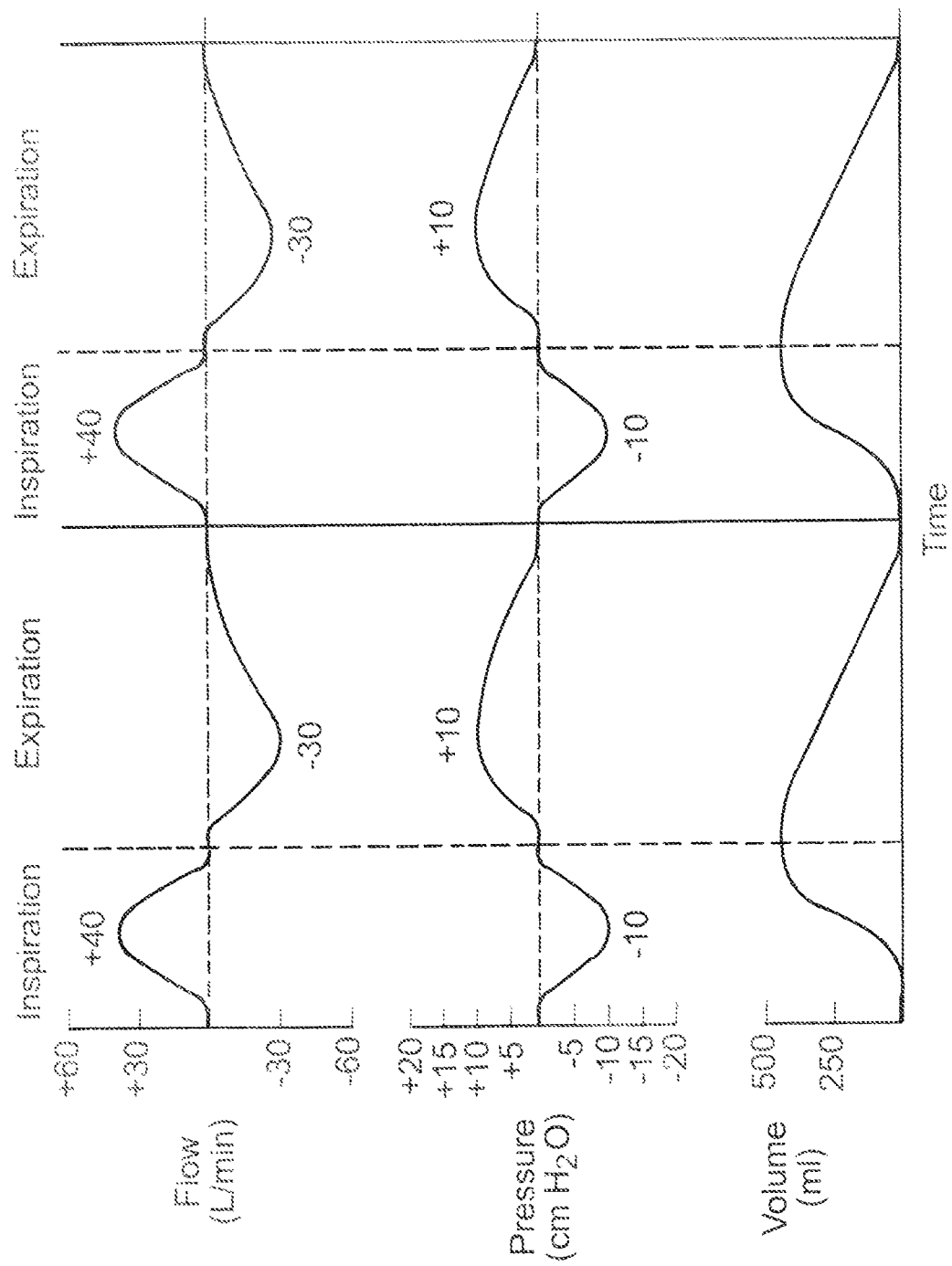
FIG. 23 is a set of graphs showing the respiratory mechanics in a patient in respiratory distress due to an exacerbation of emphysema with bronchitis.
Figure 24:
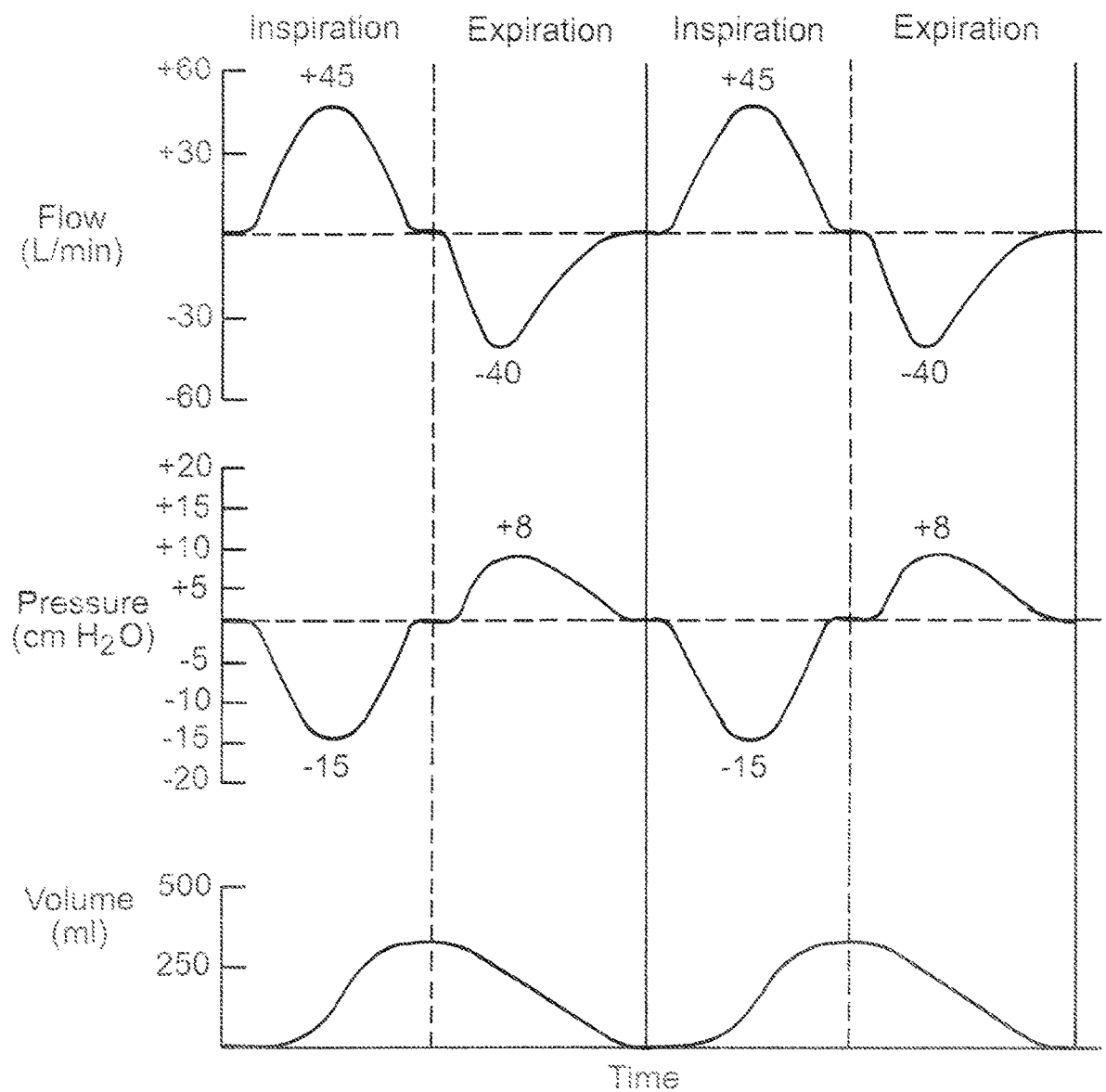
FIG. 24 is a set of graphs showing the respiratory mechanics for a patient with Adult Respiratory Distress Syndrome (ARDS).
Figure 25:
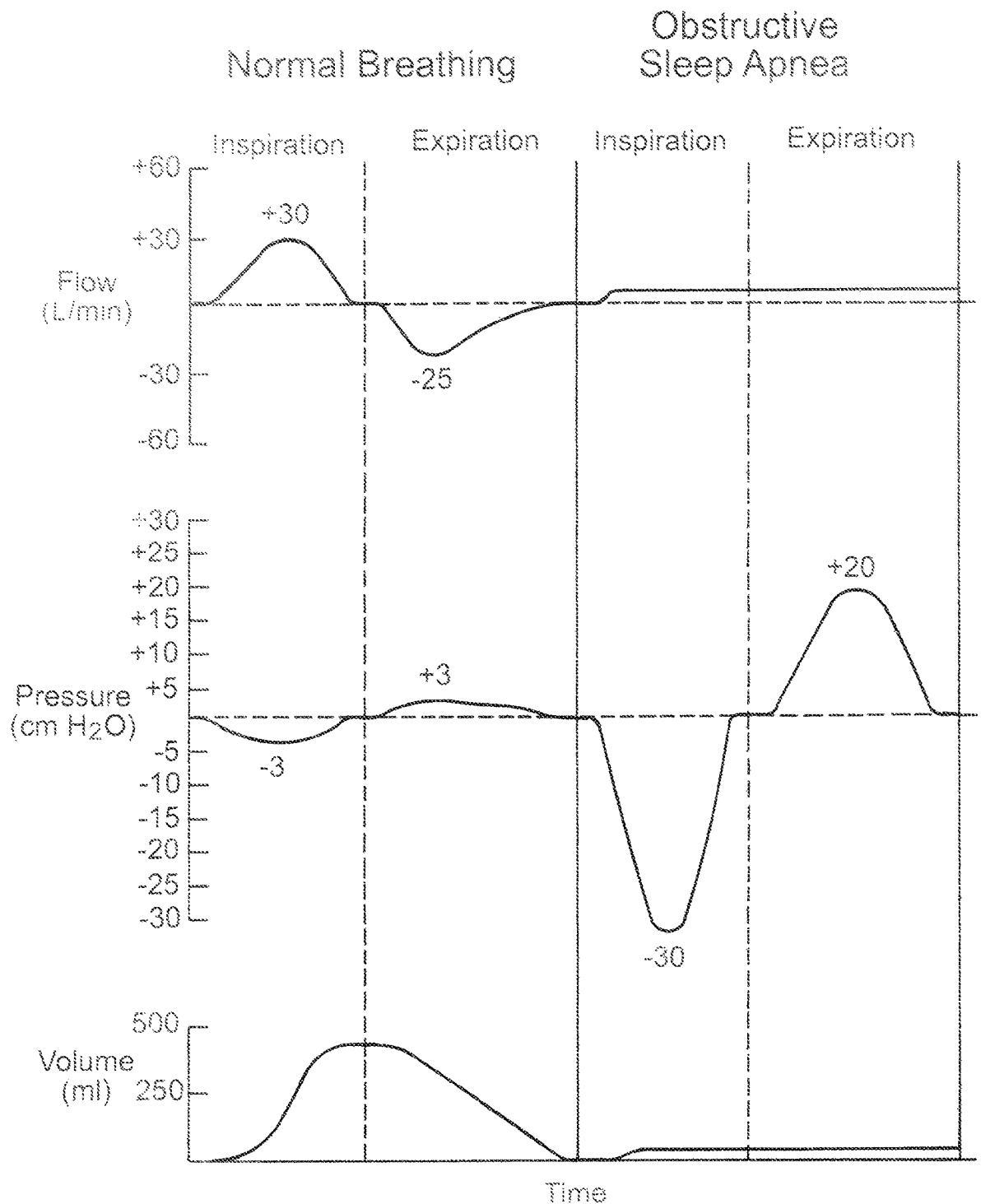
FIG. 25 is a set of graphs showing the respiratory mechanics for a patient with obstructive sleep apnea with respiratory distress.

The following discussions and accompanying FIGS. 23-25 present examples of pathophysiology of a number of diseases and disorders that may benefit from use of the present invention. Application of the invention is by no means limited to these examples of diseases and disorders.

FIG. 23 shows contrasting respiratory mechanics in a self-breathing patient in respiratory distress due to an exacerbation of emphysema with bronchitis. Increased airway resistance resulting from bronchial airway obstruction directly increases inspiratory WOB. The over-distended diseased lung is difficult to inflate and inspiratory WOB is increased. Consequently, the airway pressure curve swings significantly more negative throughout the sinusoidal inspiratory phase, due to increased inspiratory WOB. Patients have difficulty drawing the breath down into the deep alveolar regions of the lungs where oxygen uptake occurs. Since the respiratory muscles in emphysema patients do not perform normally, there is a limit to how much extra work can be performed. Though pressure may transiently return to zero during the phase between inspiration and expiration, the airways are so collapsed and obstructed that significant expiratory WOB is required to allow the trapped breath to be exhaled. Patients purse their lips and close their vocal cords (which do not require much energy) and then forcefully engage their expiratory respiratory muscles to build up back-pressure required to mechanically dilate the airways so that obstruction can be improved and exhalation can more effectively occur in this disease state. Consequently, expiratory pressures are elevated even during normal negative pressure breathing that occurs without positive pressure mechanical ventilation. The patient also tries to allow more time for trapped gas to be exhaled, so even though the time required for inspiration is little changed, proportionately more time is spent in exhalation (1:2 ratio). This requires a slower respiratory rate. If this can not occur, air trapping (hyperinflation) results. This inefficient breathing pattern causes worsening gas exchange and mechanics and further increases in WOB.

In addition to requirements for increased inspiratory and expiratory WOB, other physiologic derangements in patients with emphysema are hypoxemia, increased physiologic dead space and reduced alveolar ventilation. Destruction of the alveoli (air sacs) and related blood vasculature and airway disease impair the effectiveness and efficiency of gas exchange, resulting in reduced uptake of oxygen and elimination of carbon dioxide. Due to the disease, patients have mismatch where the areas of ventilation don't adequately match blood flow, so inadequate oxygen enters the body (hypoxemia). Additionally, there are many bronchial tubes that lead to diseased alveolar sacs where there is ventilation, but completely inadequate blood flow. Consequently, ventilation is wasted and there is increased dead space due to completely inadequate gas exchange. Consequently, for a given tidal breath in, a higher than normal portion of it does not get to the alveolar sacs where oxygen can be taken up and carbon dioxide can be released from the blood stream (inadequate alveolar ventilation). Additionally, during the last component of the expiratory phase, some of the carbon dioxide does not get exhaled into the atmosphere and is trapped in the airways (trachea, bronchial tubes, pharynx, oral and nasal cavity) and alveolar sacs without blood flow (physiologic dead space). Patients with increased physiologic dead space, as in this example, have more trapped carbon dioxide that is breathed in to the alveolar sacs again during the first component of the next inspiratory phase. The self-breathing patient has few choices; either increase the respiratory rate and/or tidal volume in an effort to try to get more minute ventilation to functioning alveolar sacs (this requires an even further increase in WOB), or to give in to excessive WOB and retain carbon dioxide in the blood (develop worsening respiratory acidosis, or respiratory failure). The present system is uniquely positioned to improve or correct these physiologic abnormalities while still allowing the patient to spontaneously self-breathe without CSPPV. This presentation of a patient with respiratory distress due to an exacerbation of emphysema is intended to illustrate one end of the spectrum of respiratory compromise with one example of a disorder where specific physiologic abnormalities occur and can be tied to a specific phase or component of a phase in the self-breathing cycle.

Negative-pressure self-breathing in a neurologic or neuromuscular disease patient with respiratory distress should also be considered. Patients with spine or brain injury and those with neuromuscular disorders can have significant respiratory distress due to impaired neurologic respiratory drive to breathe or due to the fact that the respiratory muscles are unable to generate adequate WOB. The respiratory mechanics would have a similar pattern to the healthy person in FIG. 22 except that adequate negative pressures may not be sustained during negative pressure self-breathing. Consequently, air flow and the tidal volume decrease. The low tidal volume results in a high dead space to tidal volume ratio, and functioning alveolar sacs receive inadequate alveolar ventilation. Elevated carbon dioxide and low blood oxygen levels can result. Mismatches in blood flow and gas in alveolar sacs can further compromise blood oxygen levels. The present invention is uniquely positioned to improve or correct these physiologic abnormalities while minimizing required WOB and still allowing the patient to spontaneously self-breathe without CSPPV.

FIG. 24 illustrates a patient on the other end of the spectrum of respiratory compromise with one example of a disorder called Adult Respiratory Distress Syndrome (ARDS). The self-breathing pattern is different than FIG. 22. The ARDS patient has some common features with the patient in FIG. 24, but also some very different pathophysiologic derangements. Unlike the over-stretched and poorly elastic lung in emphysema, ARDS causes a very stiff lung that is difficult to inflate and the lungs have blood flow that is shunted around alveolar sacs that are collapsed or full of fluid (congestive atelectasis). Consequently, very little oxygen gets to the lungs and the patient is driven to breathe deep and fast to attempt to get more oxygen into functional alveolar sacs to compensate. Though still inspiring with a normal sinusoidal negative pressure swing during the inspiratory phase of breathing, the negative pressure pattern is pronounced due to the high inspiratory WOB required to inflate the stiff lungs with the high ventilatory requirements. Any reduction in either anatomic or physiologic dead space would be beneficial in reducing excessive ventilatory requirements. Patients have difficulty drawing the breath down into the deep functioning alveolar regions of the lungs where oxygen uptake can occur. Intense WOB is required. Though the elastic recoil of the stiff lung helps gas initially escape during the early expiratory phase, expiratory WOB (particularly during the later segments of the expiratory phase) is increased to force the gas out of the lungs so the expiratory time can be shorter (1:1 ratio) allowing a faster respiratory rate without significant compromise of the relationship of inspiration to the total breathing cycle (respiratory duty cycle). Pressure also swings positive during the expiratory phase as patients have increased expiratory WOB in an effort to force flow during expiration into collapsed alveolar sacs (atelectasis) for lung recruitment. The inspiratory and expiratory WOB are further driven by the respiratory center's intense stimulus to drive higher tidal volumes and faster respiratory rates. The present invention is uniquely positioned to improve or correct these physiologic abnormalities while still allowing the patient to spontaneously self-breathe without CSPPV.

FIG. 25 shows respiratory mechanics during negative-pressure self-breathing in a patient with obstructive sleep apnea with respiratory distress. A normal respiratory cycle during sleep where obstruction is not present is illustrated on the left. It is similar to FIG. 22. However, in an iterative cyclic fashion, the upper airway totally obstructs, resulting in the absence of inspiratory flow and absence of inspiratory volume. Large negative pressure values are generated as the patient struggles to inspire. Similarly, the patient forcefully attempts to exhale against the obstructed upper airway and significant expiratory pressures are generated, but flow is curtailed and there is no inspired tidal volume to exhale. The obstruction is aggravated because upper airway tissue is sucked together by the stronger and stronger negative pressure efforts and "obstruction begets obstruction" because nothing is stenting the opposing tissues to keep them apart as negative pressure efforts increase. Abnormalities in oxygen and carbon dioxide exchange occur and cardiovascular and neurologic impairment with severely disrupted sleep architecture are problematic.

Continuous Positive Airway Pressure (CPAP), which is a form of CSPPV, uses pressure to prevent obstruction with sleep apnea patients and to prevent large negative pressure swings. Similarly, the present system is uniquely positioned to improve or correct these physiologic abnormalities while still allowing the patient to spontaneously self-breathe without the need for CPAP and associated discomforts and complications encountered with CSPPV. Sleep apnea patients can have central episodes, where there are iterative periods throughout sleep where no efforts are made to breathe. Patients have breathing cycles with no upper airway obstruction, but the absence of flow, volume and pressure are noted. The problems are getting adequate oxygen deep into the alveolar units where oxygen uptake can occur and getting carbon dioxide expelled into the atmosphere. The present invention is uniquely positioned to improve or correct these physiologic abnormalities while still allowing the patient to spontaneously self-breathe without the need for CPAP and associated discomforts and complications encountered with CSPPV.

The following discussions and FIGS. 26-33 serve to specifically demonstrate how using an open system to provide pressure-mitigating, breath-synchronized, flow-targeted ventilation can improve physiology in self-breathing patients with the previously described diseases and disorders. As stated previously, use of the invention is not limited to these disease and disorder examples. Furthermore, these example figures are not intended to limit the scope of the invention. It should be noted that the flow waveforms and associated flow rates of oxygen-containing gas delivered through the airway interface 60 should be sufficient to achieve the desired physiological benefit for the patient, such as reducing the patient's work of breathing by reducing the airway pressure that the patient must generate during spontaneous breathing, flushing carbon dioxide from the patient's airway, and increasing ventilation and improving blood oxygenation. This typically requires a peak flow rate in the approximate range of 7 to 60 L/min for adults, and proportionally reduced peak flow rates for pediatric and infant populations. The inspiratory and expiratory flow waveforms and related flow rates associated with phases of the inspiratory and expiratory respiratory cycle are examples only. Required flow rates and waveforms may change from time to time in the management of an individual. Similarly, required flow rates and waveforms will vary based upon the management of adult, child or infant populations.

Figure 26:
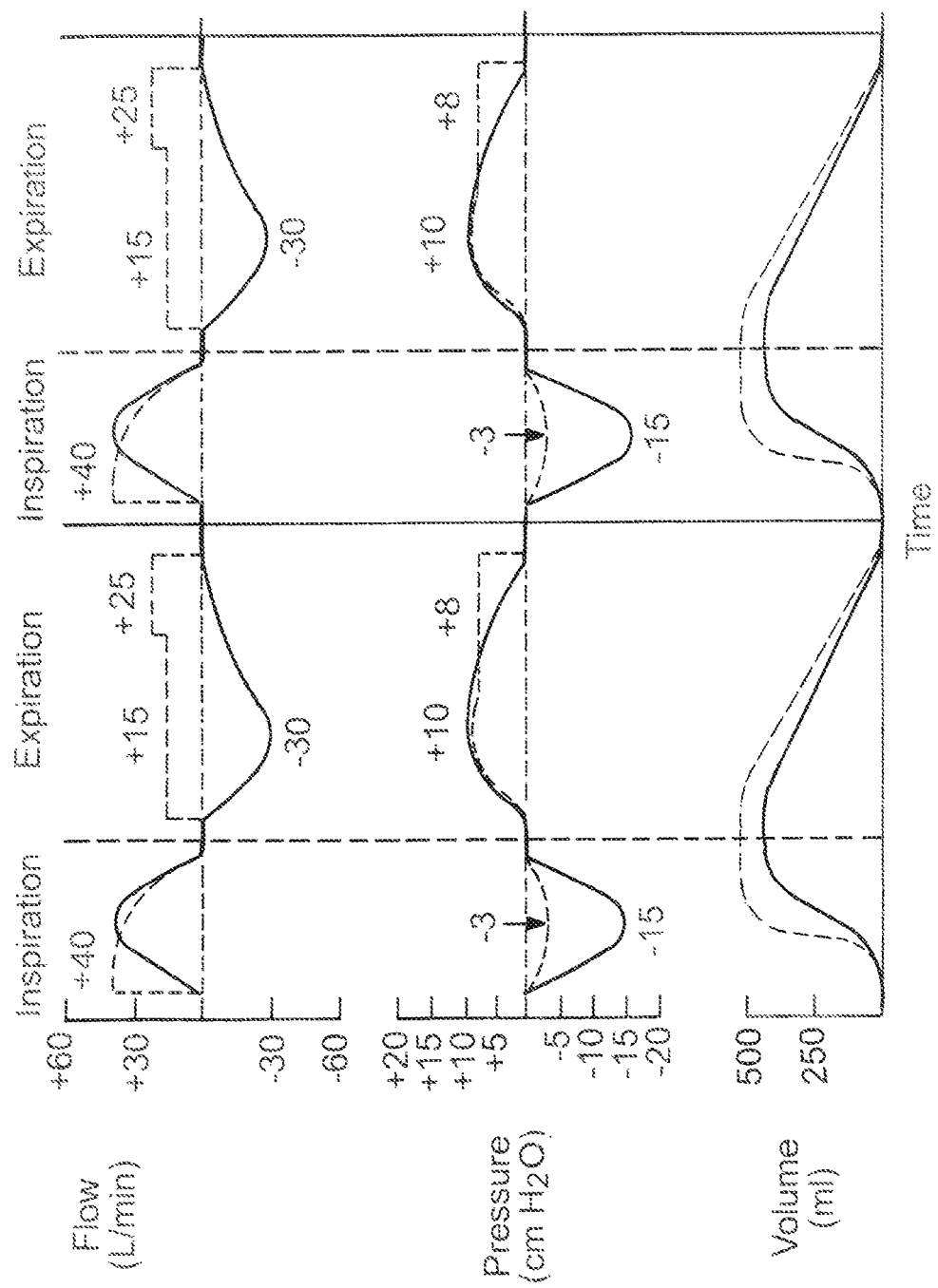
FIG. 26 is a set of graphs illustrating breathing in an emphysema patient in respiratory distress treated using the present invention to provide interrupted flow-targeted ventilation.

FIG. 26 illustrates negative-pressure self-breathing in an emphysema patient in respiratory distress treated using the present invention to provide interrupted flow-targeted ventilation (Example 1). FIG. 26 and others that follow show two respiratory cycles of the previous examples of impaired respiratory mechanics in patients with respiratory distress due to different respiratory disorders with specific pathophysiologic derangements that have been previously defined. A key element is that the present invention supports the normal self-breathing process while either eliminating or minimizing problems encountered with prior art systems.

As previously mentioned, there are four phases to the respiratory cycle. There is a transition phase between expiration and inspiration, which is followed by the inspiratory phase. Similarly, there is a transition phase between inspiration and expiration which is followed by the expiratory phase. Furthermore, there are components within the inspiratory and expiratory phases. The flow, pressure and volume generated with the patient's unsupported self-breathing in FIG. 26 are illustrated on the vertical axis in solid lines. Intervention with peak flows and flow patterns delivered by the invention that are superimposed upon the respiratory cycle of the self-breathing patient in an open system is demonstrated in dashed lines. Expected clinical response with respect to alterations of patient pressure patterns achieved as a result of superimposed targeted flows delivered by the invention is shown in dashed lines. Dashed lines also reflect the anticipated increases in tidal volume resulting from use of the invention. Other anticipated physiologic outcomes of the invention are discussed. In this particular example there is interrupted flow delivery in the transition between expiration and inspiration and between inspiration and expiration that matches a normal breathing pattern.

FIG. 26 shows a rapidly accelerating inspiratory flow with a peak of 40 cm H2O. The initial accelerated flow is synchronized with the patient's initial inspiratory effort in the very first component of the inspiratory phase. The early onset of a high flow that exceeds the requirement of the normal breathing pattern facilitates delivery of gas deep into functional alveolar gas exchange units which results in improved alveolar ventilation and consequently improved oxygen uptake and carbon dioxide elimination. Flow during the very early component of the inspiratory phase has maximum impact upon oxygen delivery during self-breathing. Following the accelerated inspiratory flow during the early inspiratory phase, the pattern transforms into a convex decelerating pattern that overlays a sinusoidal flow pattern of the patient's breath during mid to late inspiration. The rapidly accelerating peak inspiratory flow (+40 L/min peak in FIG. 26) and flow pattern reduces inspiratory WOB because the device delivers flow on the leading edge of the breath and less respiratory muscular work is required to physically draw the gas into the lungs. The decelerating flow pattern superimposed upon the patient's diminishing flow supports the diminishing needs for work to be performed during the remainder of the inspiratory phase. The inspiratory flow supplied by the present system also enhances alveolar ventilation during this phase of the patient's respiratory cycle and tidal volume is increased.

FIG. 26 demonstrates a reduction in the inspiratory negative-pressure swing, which indicates reduced inspiratory WOB. In other words, the negative pressure required by the patient to inspire is mitigated by use of the device's targeted flow pattern. Because of the open design of the system, positive pressure during inspiration does not occur because any gas that is not inhaled can easily escape into the atmosphere, mitigating positive pressure buildup. At the onset of expiration, a flow of 15 L/min is triggered in this example and a rectangular flow pattern continues through early and mid exhalation. Patients with emphysema purse their lips and vocal cords throughout exhalation (which requires negligible work) and then use the work of the expiratory muscles to build up back-pressure to mechanically dilate diseased airways to facilitate exhalation. The expiratory flow and flow pattern delivered by the device mechanically dilates the diseased airways and mitigates the pressure that the patient would otherwise generate by increased WOB. During the late component of exhalation the peak flow with the rectangular flow pattern is increased to 25 L/min. This flow boost continues to further mechanically dilate the airways to prevent distal airway collapse, but also flushes out the carbon dioxide that collects in the anatomic and physiologic dead space areas at the end of exhalation. Carbon dioxide is washed out and replaced by oxygen enriched gas that will be available to functioning alveoli on the next breath.

Additional flow provided by the invention during exhalation allows the self-breathing patient more effective and efficient use of the expiratory muscles, vocal cords, pharynx and lips to facilitate normal quality, non-fatiguing speech. Similarly, additional flow provided by the invention during exhalation allows the self-breathing patient to increase cough effectiveness by increasing flow during the expulsive phase of cough. Additional flow provided by the invention during exhalation allows the self-breathing patient more effective and efficient use of the vocal cords and lips in maximizing the physiologic effects related to the rate at which gas exits the chest. Different flow rates and flow patterns administered during the expiratory phase that are illustrated in the following examples may also result in these benefits in a variety of patient populations.

Figure 27:
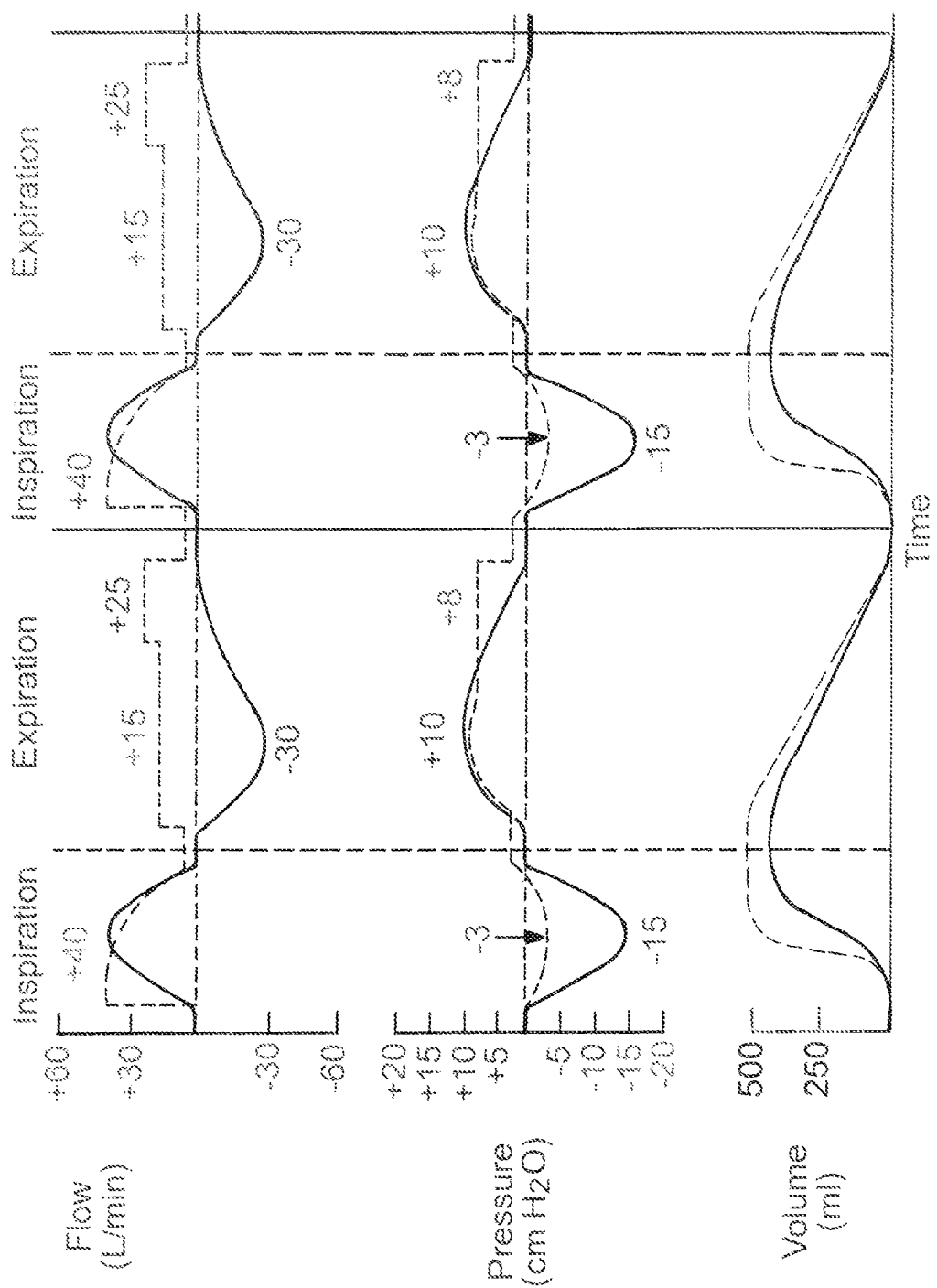
FIG. 27 is a set of graphs illustrating breathing in an emphysema patient in respiratory distress treated using the present system with an alternative waveform to deliver continuous flow-targeted ventilation.

FIG. 27 illustrates negative-pressure self-breathing in an emphysema patient in respiratory distress treated using the present system to deliver continuous flow-targeted ventilation (Example 2). The only difference in application of the invention between the patient management in FIG. 26 versus FIG. 27 is that the flow is not interrupted during the transition between exhalation and inhalation or in the transition between inhalation and exhalation. Based upon a patient-specific condition for a variety of disorders, continuous flow may or may not be advantageous. Continuous flow may also be used with any of the examples demonstrating interrupted flow.

Figure 28:
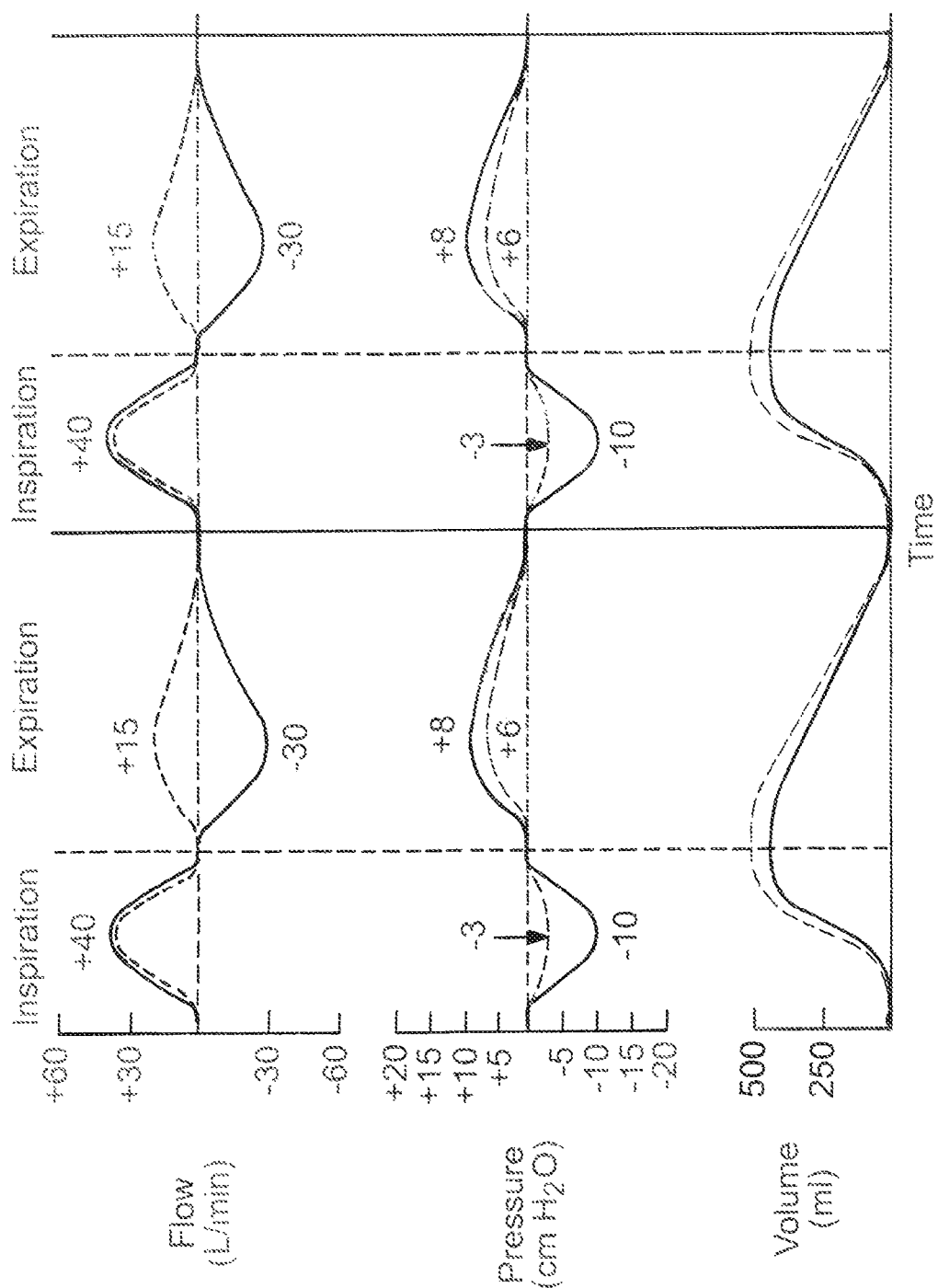
FIG. 28 is a set of graphs illustrating breathing in an emphysema patient in mild respiratory distress treated using the present invention to deliver with interrupted flow-targeted ventilation.

FIG. 28 illustrates negative-pressure self-breathing in an emphysema patient in mild respiratory distress treated using the present invention to deliver interrupted flow-targeted ventilation (Example 3). In this example of the implementation of the invention the patient is determined by the physician to be less compromised and requires less aggressive support. The application delivers a peak flow and flow pattern to mimic the sinusoidal inspiratory and expiratory flow patterns of the self-breathing patient. Reduced WOB on inspiration and expiration occur, alveolar ventilation is supported, and airway collapse is treated. Similarly, this flow-targeted ventilation with this flow pattern is likely to be beneficial for self-breathing patients with neurologic or neuromuscular diseases. The physiologic derangements in this patient population have been previously described. These individuals should benefit from the present invention.

Figure 29:
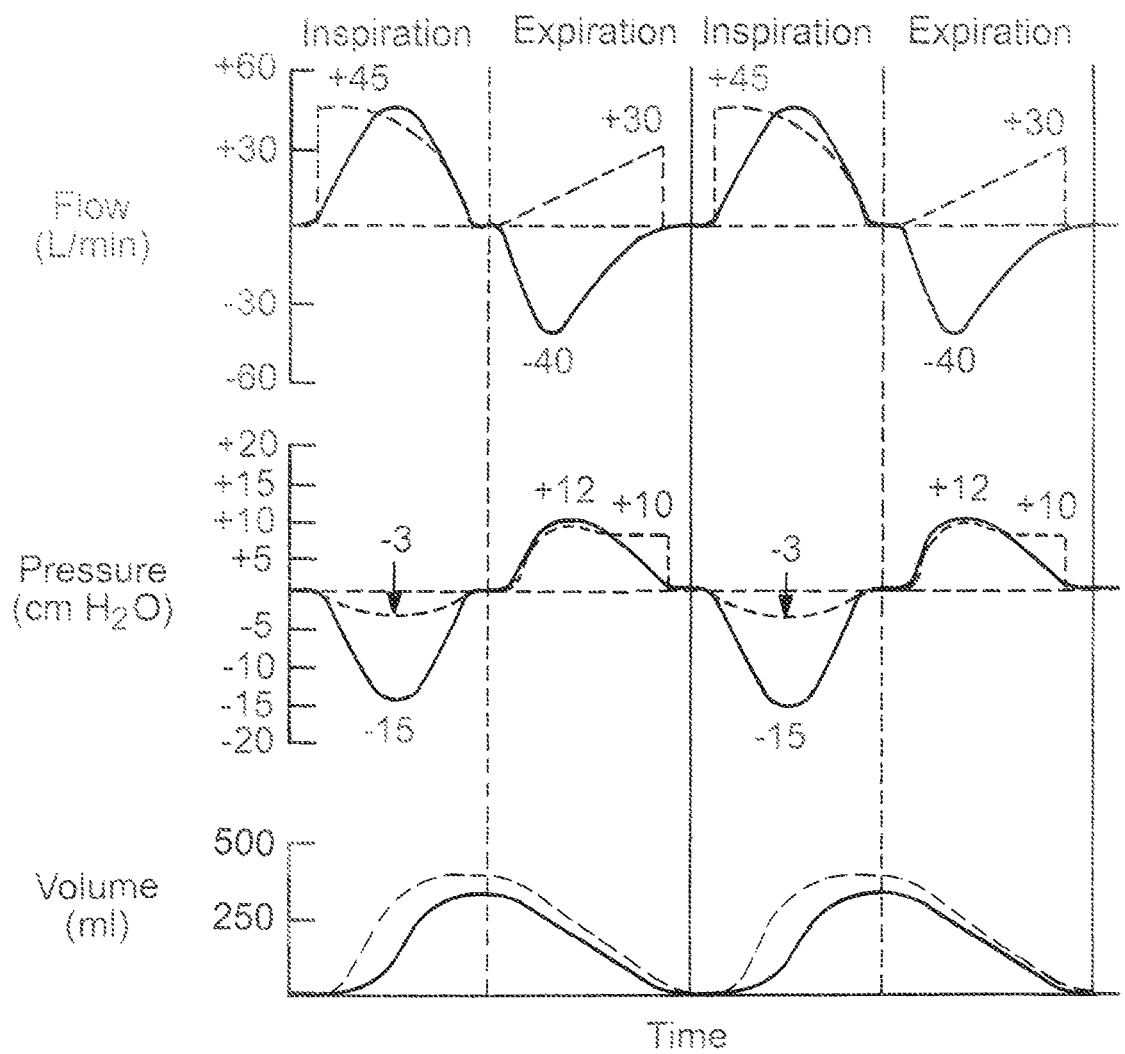
FIG. 29 is a set of graphs depicting breathing in an ARDS patient in respiratory distress treated with the present system to provide interrupted flow-targeted ventilation.

FIG. 29 depicts negative-pressure self-breathing in an ARDS patient in respiratory distress treated with the present system to provide interrupted flow-targeted ventilation (Example 4). FIG. 29 shows a rapidly accelerating inspiratory flow (with a peak of 45 cm H2O in this example). The initial accelerated flow is synchronized with the patient's initial inspiratory effort in the very first component of the inspiratory phase. The early onset of a high flow that exceeds requirements of the normal breathing pattern facilitates delivery of gas deep into functional alveolar gas exchange units, which results in improved ventilation to alveolar sacs causing improved oxygen uptake and carbon dioxide elimination. Flow during the very early component of the inspiratory phase has maximum impact upon oxygen delivery during self-breathing. Failure of adequate uptake of oxygen in spite of administration of a gas with a high percentage of oxygen (refractory hypoxemia) is a derangement in ARDS that should be improved by the present invention, particularly with this flow pattern that is also designed to recruit collapsed alveolar sacs. Following the accelerated inspiratory flow during the early inspiratory phase, the pattern transforms into a convex decelerating pattern that overlays sinusoidal flow pattern of the patient's breath during mid to late inspiration. The rapidly accelerating peak inspiratory flow and flow pattern reduces inspiratory WOB because the device delivers flow on the leading edge of the breath and less respiratory muscular work is required to physically draw the gas deep into the lungs. The first portion of the inspiratory phase in ARDS requires the most WOB because the stiff lungs characteristic of this disorder are most stiff (highest elastic recoil) at lowest lung volumes encountered at the beginning of inspiration. FIG. 29 demonstrates a reduction in the inspiratory negative pressure swing, which indicates reduced inspiratory WOB. In other words, the negative pressure required by the patient to inspire is mitigated by use of the device's targeted flow pattern. Because of the open design of the system, positive pressure during inspiration does not occur because any gas that is not inhaled can easily escape into the atmosphere, mitigating positive pressure buildup.

Patients with ARDS, due to the high elastic recoil created by the disorder, are generally able to passively exhale gas from the lungs. However, with the tendency of alveolar sacs to collapse, administration of flow during exhalation can be beneficial in preventing further atelectasis (alveolar collapse) or even opening collapsed alveolar sacs (recruitment). The ARDS patient requires a high minute ventilation. Though excessive physiologic dead space may not be present, any reduction in physiologic and/or anatomic dead space can reduce ventilatory requirements during self-breathing. The elevated flow achieved at end-expiration with this flow-targeted pattern is designed to meet those needs through carbon dioxide wash out.

Figure 30:
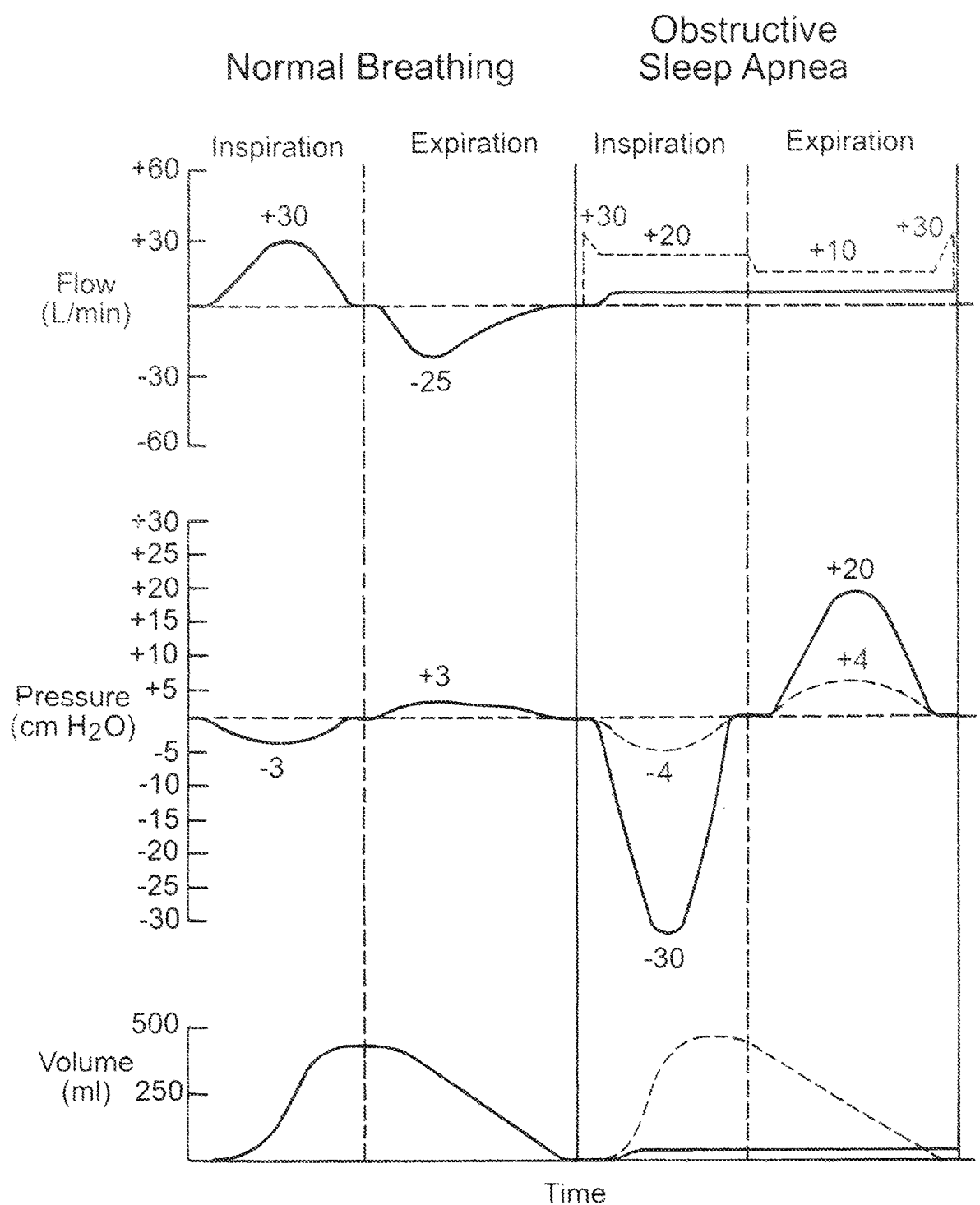
FIG. 30 illustrates breathing in an obstructive sleep apnea patient in respiratory distress treated with the present system.

FIG. 30 (Example 5) illustrates negative-pressure self-breathing in an obstructive sleep apnea patient in respiratory distress treated with the present system. Upper airway collapse and the physiologic derangements in obstructive sleep apnea have been previously described. In the treatment of obstructive sleep apnea, the present system can be used to target a flow pattern with flow rates that maintain patency or openness of the upper airway during self-breathing. The flow rate (and pattern) required to achieve and maintain patency or openness may be different relative to the phase or component of the phase of the respiratory cycle and requirements may vary from individual to individual.

FIG. 30 illustrates an example where an initial high flow at the onset of inspiration occurs to prevent upper airway collapse during the initial negative pressure generated at the onset of inspiration. Though the flow pattern tapers during mid to late inspiration, relatively high flows are maintained to prevent inspiratory upper airway collapse, which results in increase inspiratory WOB. The mitigation of increased inspiratory negative pressures prevents obstruction from begetting obstruction. Similarly, relatively high flows are maintained during the expiratory phase though flows are of less magnitude. These flows also stent the airway during exhalation and prevent the floppy upper airway tissues from causing obstruction. Accelerated flow occurs towards the end of exhalation in order to maintain patency prior to the onset of the next negative pressure swing at the onset of inspiration. This is an example where continuous flow, rather than interrupted flow, may be the preferred method as it may be more effective in preventing upper airway collapse in obstructive sleep apnea. Unlike bi-level positive pressure ventilation or continuous positive airway pressure, a partial obstruction between the upper airway and atmosphere is not required. Patients self-breathe with an open system. Complications and discomforts of CSPPV systems are avoided. Relief and prevention of obstruction prevents the physiologic derangements associated with the disorder. For patients with central sleep apnea, flow patterns shown in FIGS. 26 and 27 should be effective in improving the physiologic derangements.

Figure 31:
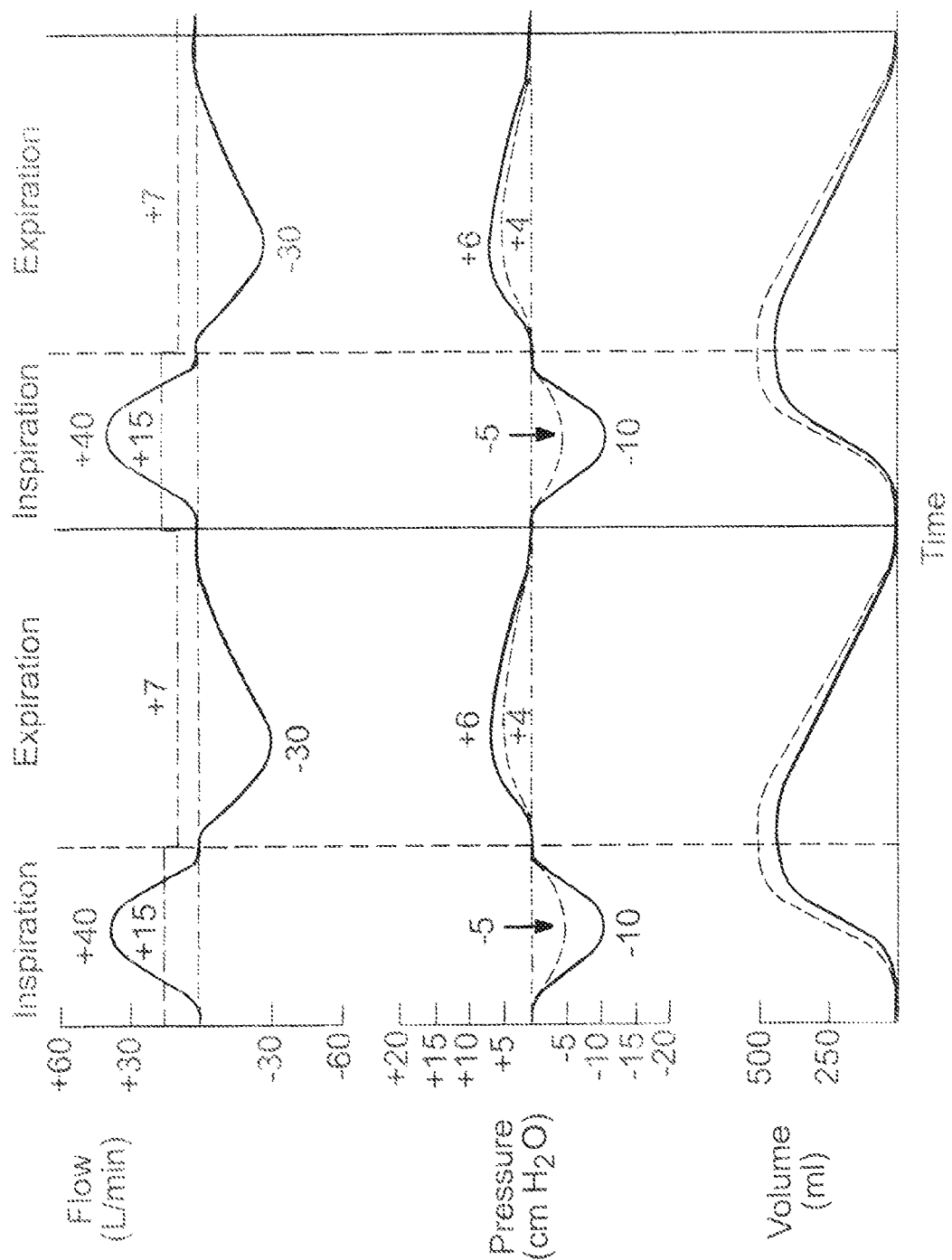
FIG. 31 illustrates breathing in an emphysema patient in mild respiratory distress treated using the present system with another alternative waveform to deliver uninterrupted flow-targeted ventilation.

FIG. 31 (Example 6) illustrates negative-pressure self-breathing in an emphysema patient in mild respiratory distress treated using the present system to deliver uninterrupted flow-targeted ventilation. In this example of an implementation of the invention, the patient is also determined by the physician to be less compromised and requires less aggressive support. However, the support is designed to augment self-breathing. A flow of 15 L/min is selected to be administered throughout the inspiratory phase and a flow of 7 L/min is selected to be administered throughout the expiratory phase. Thus, flow-targeted ventilation is synchronized with the respiratory cycle and results in a flow pattern that is not the same constant flow throughout the entire respiratory cycle. The higher inspiratory flow is designed to augment the inspiratory breath and the lower expiratory flow is designed to facilitate speech and glottic functioning and to prevent airway collapse and wash out dead space without providing excessive expiratory flows for this particular patient. Flow is uninterrupted during transitions between inspiration and expiration and between expiration and inspiration.

Figure 32:
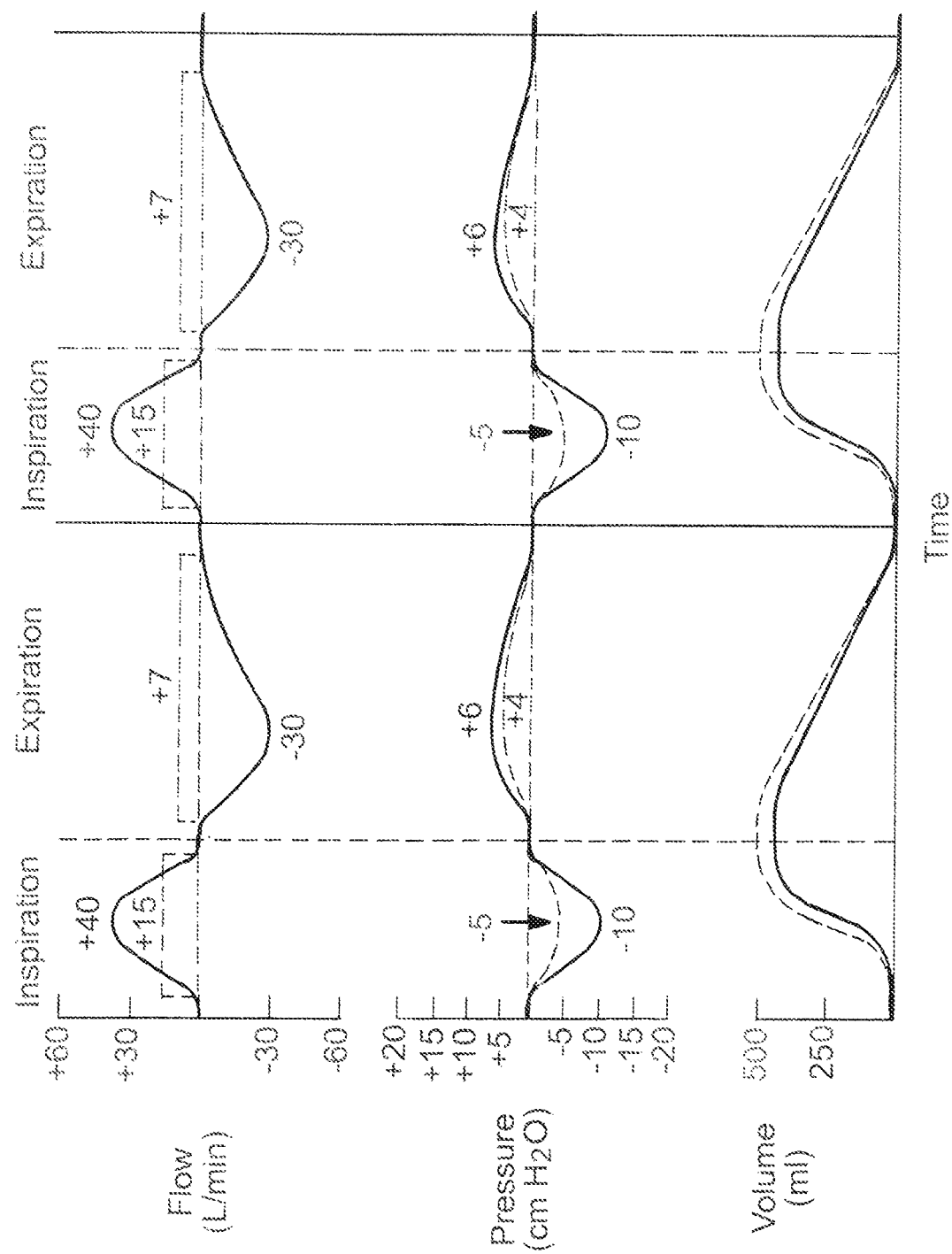
FIG. 32 illustrates breathing in an emphysema patient in mild respiratory distress treated with the present invention supplying interrupted flow-targeted ventilation with modification of the alternative waveform of FIG. 31.

FIG. 32 illustrates negative-pressure self-breathing in an emphysema patient in mild respiratory distress treated with the present invention supplying interrupted flow-targeted ventilation (Example 7). Similar to the example in FIG. 31 with the implementation of the invention, the patient is also determined by the physician to be less compromised and requires less aggressive support. However, the support is designed to augment self-breathing. A flow of 15 L/min is selected to be administered throughout the inspiratory phase and a flow of 7 L/min is selected to be administered throughout the expiratory phase. Thus, flow-targeted ventilation is synchronized with the respiratory cycle and results in a flow pattern that is not constant throughout the entire respiratory cycle. The higher inspiratory flow is designed to augment the inspiratory breath and the lower expiratory flow is designed to facilitate speech and glottic functioning, to prevent airway collapse and wash out dead space without providing excessive expiratory flows for this particular patient. The difference is that flow is interrupted during transitions between inspiration and expiration and between expiration and inspiration.

Figure 33:
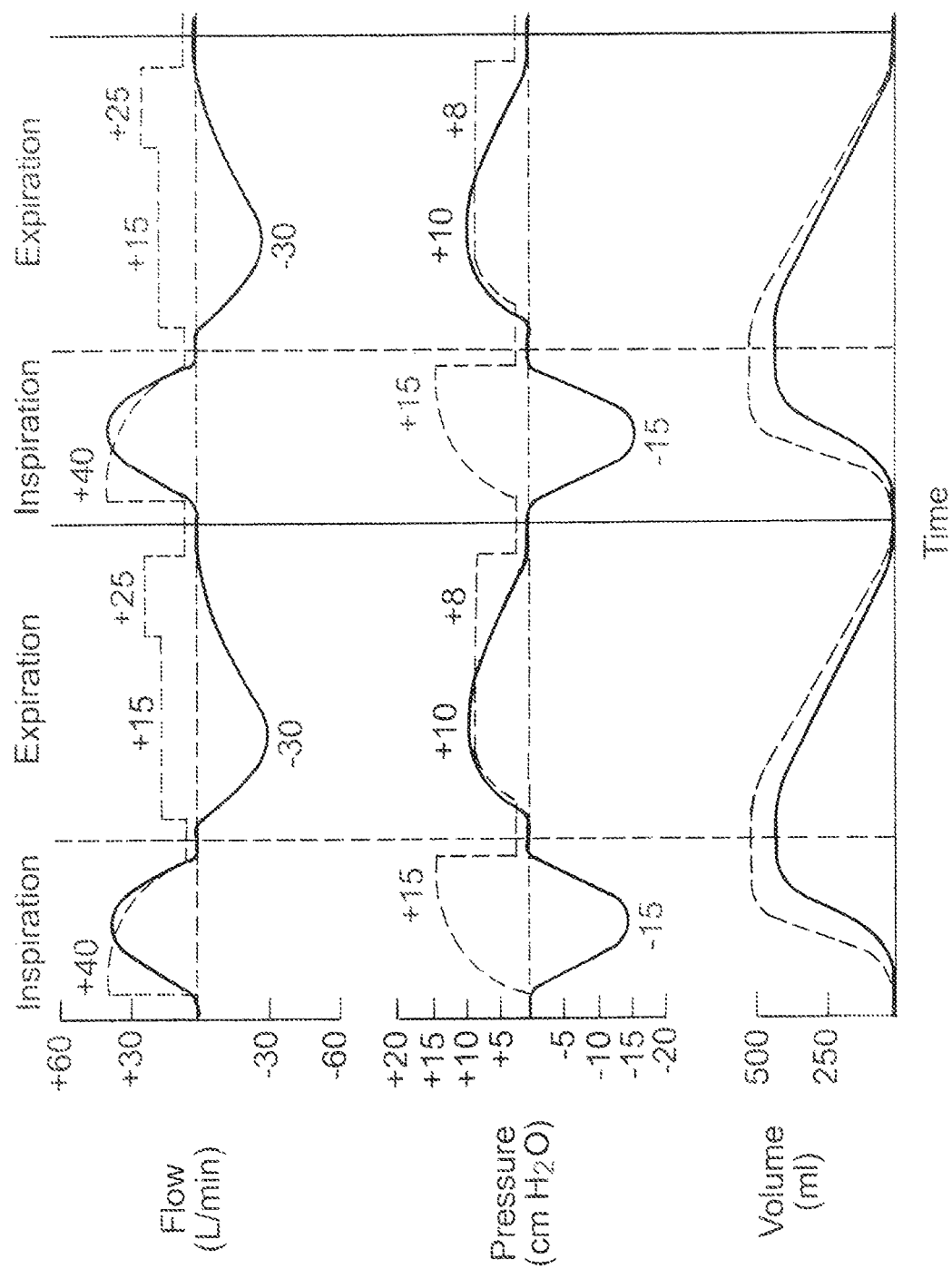
FIG. 33 illustrates breathing in an emphysema patient in mild respiratory distress treated using the present invention with continuous flow-targeted ventilation and patient control of passive inflation.

FIG. 33 illustrates negative-pressure self-breathing in an emphysema patient in mild respiratory distress treated using the present invention with continuous flow-targeted ventilation and patient control of passive inflation (Example 8). As noted previously, patients with lung disease may use their vocal cords to control or regulate flow in and out of the lungs. Additionally, patients may also "purse" or close their lips to control respiratory flow. This requires little effort. Certain patients may benefit if they learn to close their vocal cords and purse their lips on inspiration, and rather than using negative pressure generated through WOB by the respiratory muscles, they would allow the flow of gas from the present system to passively and effortlessly inflate the lungs. Unlike CSPPV, where the device determines when the breath is triggered on or inspiration is cycled off, the self-breathing patient controls the respiratory cycle in BSFTV mode.

FIG. 33 demonstrates an emphysema patient in respiratory distress where, due to closure of the vocal cords or mouth on inspiration, the flow from the device passively inflates the lungs. Negative pressure otherwise required to inflate the lungs by the self-breathing patient's respiratory muscles is mitigated. The flow pattern is similar to FIG. 27 where the fast ramp-up allows the patient to promptly inflate the lungs, allowing more time for exhalation. Adequate time to exhale is beneficial. Little or no work is required by the diaphragm or other inspiratory muscles. Though positive pressure is achieved on inspiration, no pressure delivered by the device is targeted and the patient determines when the pressure is relieved by opening the vocal cords and lips. Partial closure of the lips and vocal cords during the expiratory phase and resulting physiologic benefits have been described. Other targeted inspiratory flows and flow patterns may be beneficial in this patient population.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A method for selectively administering either closed-system positive-pressure ventilation (CSPPV) or breath-synchronized flow-targeted ventilation (BSFTV) to a patient having a tracheal tube with an inflatable cuff, said method comprising:

providing a ventilator selectively delivering either CSPPV or BSFTV to the patient via a ventilator hose;

in CSPPV mode, connecting the ventilator hose to the proximal end of the tracheal tube and operating the ventilator to provide closed-system positive-pressure ventilation to the patient through the tracheal tube;

in BSFTV mode:
(a) providing an adaptor having: (i) a cap with a first connector for removable attachment to the ventilator hose, and a second connector for removable attachment to the proximal end of the tracheal tube; and (ii) an inner cannula extending from the cap that is removably insertable into the tracheal tube to divide the tracheal tube into a first lumen and a second lumen, with the first lumen of the tracheal tube allowing a spontaneously-breathing patient to freely inhale and exhale in open exchange with the atmosphere through the tracheal tube and adaptor;
(b) attaching the adaptor to the tracheal tube by inserting the inner cannula into the tracheal tube and attaching the second connector of the adaptor cap to the proximal end of the tracheal tube; and
(c) providing a sensor for detecting a physical property of the patient's respiratory cycle;

in the BSFTV mode, attaching the ventilator hose to the first connector of the adaptor cap, and operating the ventilator to deliver a flow of oxygen-containing gas to the patient through the adaptor cap and the second lumen of the tracheal tube to augment a patient's spontaneous respiration, said delivered flow varying over each inspiratory and expiratory phase of the respiratory cycle in a predetermined non-constant flow waveform synchronized with the respiratory cycle as detected by the sensor to augment the patient's spontaneous respiration having:
(a) a positive flow accelerating at the onset of the patient's inspiratory phase at a flow rate sufficient to significantly mitigate the airway pressure the patient must generate during spontaneous breathing and thereby reduce the patient's work of breathing; and
(b) a positive flow during at least the early portion of the patient's expiratory phase at a flow rate sufficient to significantly mitigate the airway pressure the patient must generate during spontaneous breathing and thereby reduce the patient's work of breathing, and to wash carbon dioxide from the patient's airway;

said delivered flow allowing a spontaneously-breathing patient to freely inhale and exhale in open exchange with the atmosphere through the first lumen of the tracheal tube and adaptor; and to transition from the BSFTV mode to the CSPPV mode, disconnecting the adaptor from the ventilator hose, and removing the adaptor from the tracheal tube.

2. The method of claim 1 wherein the sensor is attached to the inner cannula.

3. The method of claim 1 wherein the adaptor further comprises a gas sampling tube extending along the inner cannula leading to the sensor.

4. The method of claim 1 wherein the sensor comprises a flow sensor monitoring the patient's spontaneous respiration through the first lumen of the tracheal tube.

5. The method of claim 1 wherein the sensor comprises a thermistor the patient's spontaneous respiration through the first lumen of the tracheal tube.

6. The method of claim 1 wherein the sensor comprises a pressure transducer monitoring the patient's spontaneous respiration through the first lumen of the tracheal tube.

7. The method of claim 1 wherein the sensor comprises a carbon dioxide sensor monitoring the patient's spontaneous respiration through the first lumen of the tracheal tube.

\* \* \* \* \*